US008865634B2

(12) United States Patent
Oertling

(10) Patent No.: US 8,865,634 B2
(45) Date of Patent: Oct. 21, 2014

(54) 4-ALKYL SUBSTITUTED PYRIDINES AS ODIFEROUS SUBSTANCES

(75) Inventor: Heiko Oertling, Holzminden (DE)

(73) Assignee: Symrise AG, Holzminden (DE)

( * ) Notice: Subject to any disclaimer, the term of this patent is extended or adjusted under 35 U.S.C. 154(b) by 371 days.

(21) Appl. No.: 12/622,996

(22) Filed: Nov. 20, 2009

(65) Prior Publication Data

US 2010/0130624 A1 May 27, 2010

(30) Foreign Application Priority Data

Nov. 27, 2008 (EP) .................................... 08170153

(51) Int. Cl.

| | |
|---|---|
| ***A61K 8/49*** | (2006.01) |
| ***C11B 9/00*** | (2006.01) |
| ***A61K 8/00*** | (2006.01) |
| ***A61Q 13/00*** | (2006.01) |
| ***A61Q 15/00*** | (2006.01) |
| ***A61Q 17/04*** | (2006.01) |
| ***A61Q 5/02*** | (2006.01) |
| ***A61Q 5/12*** | (2006.01) |
| ***C11D 1/83*** | (2006.01) |
| ***C11D 3/50*** | (2006.01) |
| ***C11D 9/02*** | (2006.01) |
| ***C11D 9/44*** | (2006.01) |
| ***C11D 3/28*** | (2006.01) |

(52) U.S. Cl.

CPC .. *C11D 3/28* (2013.01); *C11D 3/50* (2013.01); *C11D 9/442* (2013.01); *C11B 9/0092* (2013.01)

USPC ................. 510/102; 510/103; 512/8; 512/10; 512/20; 514/788

(58) Field of Classification Search

USPC ............ 512/8, 20, 10; 510/102, 103; 514/788

See application file for complete search history.

(56) References Cited

U.S. PATENT DOCUMENTS

| | | | | |
|---|---|---|---|---|
| 2,247,266 | A * | 6/1941 | Wibaut et al. | 546/347 |
| 2,658,850 | A | 11/1953 | Cislak | |
| 2,712,019 | A * | 6/1955 | Tenenbaum et al. | 546/349 |
| 3,171,839 | A | 3/1965 | Rorig | |
| 3,178,435 | A * | 4/1965 | Marxer | 546/346 |
| 3,381,691 | A * | 5/1968 | Schumacher et al. | 131/276 |
| 3,517,031 | A | 6/1970 | Beereboo et al. | |
| 3,669,908 | A | 6/1972 | Hall | |
| 3,702,253 | A * | 11/1972 | Winter et al. | 426/537 |
| 4,374,051 | A * | 2/1983 | Naf et al. | 512/10 |
| 4,555,520 | A | 11/1985 | Misra et al. | |
| 5,219,847 | A * | 6/1993 | Taguchi et al. | 514/188 |
| 5,298,486 | A | 3/1994 | Thomas et al. | |
| 5,861,435 | A * | 1/1999 | Yokoi et al. | 514/570 |
| 7,934,888 | B2 * | 5/2011 | Masters et al. | 405/216 |
| 2008/0269058 | A1 * | 10/2008 | Cotterill | 504/212 |
| 2009/0185867 | A1 * | 7/2009 | Masters et al. | 405/216 |
| 2010/0130624 | A1 * | 5/2010 | Oertling | 514/788 |
| 2013/0236402 | A1 * | 9/2013 | Wiedmann et al. | 424/59 |

FOREIGN PATENT DOCUMENTS

| | | |
|---|---|---|
| EP | 0470391 A1 | 2/1992 |
| EP | 1123950 A1 | 8/2001 |

OTHER PUBLICATIONS

Akiba et al., "A Convenient Method for the Regioselective Synthesis of 4-Alkyl(aryl)pyridines Using Pyridinium Salts", Bull. Chem. Soc. Jpn., 57, 1994-1999 (1984).*

Concise Science Dictionary, Oxford University Press, 1984, p. 460, definition for "naphthalene".*

Sell C.S., "On the Unpredictability of Odor," Angewandte Chemie. International Edition, Wiley-VCH, Verlag, Weinheim, vol. 45, No. 38, Sep. 25, 2006, pp. 6254-6261, XP007911257.

Examination Report issued in EP Application No. 08 170 153.4, dated Dec. 1, 2010.

Kuang C. Yeh et al: "Oil-Water Distribution of p-Alkylpyridines", Journal of Pharmaceutical Sciences, Jan. 1, 1976, Seiten 80-86, XP55005708, Gefunden im Internet: URL:http://onlinelibrary.wiley.com/store/10.1002/jps.2600650116/asset/ 2600650116_ftp.pdf?v=1&t=grx4360r&s=c746e5e73ec4ab5bfd6f7977bde4103138a976d6 [gefunden am Aug. 29, 2011].

Wibaut J et al: "Syntheses with the Aid of y-Picolyllithium I. Preparation of 4-alkylpyridines", Recueil Des Travaux Chimiques Des Pays-Bas, Bd. 72, Jan. 1, 1953, Seiten 513-521, XP009113481.

Office Action, European Application No. 08170153.4, received Nov. 9, 2011.

*Recueil des Travaux Chimiques des Pays-Bas et de la Belgique*, 1953, 72, 513-521.

Parish Chemical Company, Orem, Utah, USA (www.parishchemical.com, see CAS No. 1815-99-2).

*Helv. Chim. Act.* 2007, 90, 1245.

*Perfumer & Flavorist*, 1994, vol. 19, Mar./Apr. 19-27.

*J. Agric. Food Chem.* 1992, 40, 2236-2243.

*Annales de Chimie*, 1944, 19, 487-521 on p. 509.

(Continued)

*Primary Examiner* — Douglas McGinty
(74) *Attorney, Agent, or Firm* — Dilworth & Barrese LLP

(57) ABSTRACT

The present invention primarily concerns certain 4-alkyl pyridines of the following formula (I), (I)

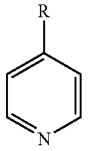

wherein R is $C_8$-$C_{12}$ alkyl, odiferous substance mixtures and aromatic substance mixtures containing these 4-alkyl pyridines, the respective uses thereof as an odiferous or aromatic substance (mixture) and corresponding perfumed products.

18 Claims, No Drawings

(56) References Cited

OTHER PUBLICATIONS

*Eur. J. Org. Chem.* 2004, 835-849.
Langmuir (2001), 1054-1059.
Journal of Solid State Chemistry 1987, 69, 145-152.
Office Action, Chinese Application No. 2012052401054420, dated May 29, 2012.
Office Action, Chinese Application No. 2013020600875610, dated Feb. 16, 2013.

* cited by examiner

4-ALKYL SUBSTITUTED PYRIDINES AS ODIFEROUS SUBSTANCES

CROSS-REFERENCE TO RELATED APPLICATION

This application claims benefit of priority to EP 08 170 153.4-2108, filed on Nov. 27, 2008, which is incorporated herein by reference in its entirety.

The present invention primarily concerns certain 4-alkyl pyridines of the following formula (I), odiferous substance mixtures and aromatic substance mixtures containing these 4-alkyl pyridines, the respective uses thereof as an odiferous or aromatic substance (mixture) and corresponding perfumed products.

4-$C_8$-$C_{12}$-alkyl pyridines to be used according to the invention correspond to formula (I):

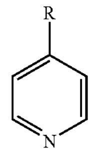

(I)

wherein

R is a branched or unbranched alkyl residue with 8 to 12 C-atoms.

R is preferably an unbranched alkyl residue with 8 to 12 C-atoms, i.e. according to the invention 4-n-$C_8$-$C_{12}$-alkyl pyridines are preferred.

In the perfume industry there is a general need for marine odiferous substances, since consumers are constantly demanding new and modern scents with watery-fresh fragrance notes. Odiferous substances with marine fragrance notes are used in large quantities and countless variations in perfumes, odiferous substance mixtures (perfume compositions) and scents for the most varied of application areas. Because of the increasing demand from consumers for new, modern fragrance notes, there is a constant need within the perfume industry for fragrances which bring about new effects in perfumes and in this way allow new fashion trends to be created. Compounds with watery-fresh fragrance notes have always been important and sought-after components in the fragrance industry. Consequently today marine odiferous substances are used in many perfume compositions.

The marine olfactory note of numerous perfume compositions is based on 7-methyl-2H-1,5-benzodioxepin-3(4H)-one (Calone 1951®). This classic marine odiferous substance is described in U.S. Pat. No. 3,517,031.

A further classic marine odiferous substance is 4-(4,8-dimethyl-3,7-nonadienyl)-pyridine (Maritima®) which is described in U.S. Pat. No. 3,669,908 and DE 2043585.

For the creation of novel modern perfume compositions there is a constant need for marine odiferous substances with special olfactory characteristics which are suitable for use as the basis for the composition of novel, modern perfumes with a complex marine character. Apart from the typical odor of the sea, the marine odiferous substances sought should exhibit further notes and aspects lending them an olfactory character and complexity.

The search for suitable marine odiferous substances, which led to the present invention, was hampered by the following issues:

- there is insufficient knowledge of the mechanisms of olfactory cognition;
- the relationships between the special olfactory cognition on the one hand and the chemical structure of the associated odiferous substances on the other have not been sufficiently explored;
- often just the slightest changes to the structural makeup of a known odiferous substance can result in major changes in the olfactory characteristics and impair the compatibility with the human organism.

The success of the search for suitable marine odiferous substances is therefore highly dependent upon the intuition of the person doing the searching.

The task for the present invention was therefore to find marine fragrances with novel olfactory characteristics, able to lend odiferous substance compositions particular olfactory notes and aspects.

It has now surprisingly been discovered that 4-$C_8$-$C_{12}$-alkyl pyridines, preferably the corresponding 4-n-alkyl pyridines, here in particular 4-decyl pyridine, are suitable for performing the task set.

Inter alia in U.S. Pat. No. 3,171,839—as an antibiotic—or *Recueil des Travaux Chimiques des Pays-Bas et de la Belgique,* 1953, 72, 513-521, the production of 4-decyl pyridine is described. Furthermore, 4-n-decyl pyridine is commercially available, e.g. under product number 1904 from the Parish Chemical Company, Orem, Utah, USA (www.parish-chemical.com, see CAS Number 1815-99-2).

Concerning the olfactory characteristics of n-alkyl pyridines in *Helv. Chim. Act.* 2007, 90, 1245 it was commented that some of these substances "[ . . . ] can have a watery profile, but this family is more reminiscent of stagnant water, sometimes with a negative connotation of wet dog".

A number of regioisomeric 3-n-alkyl pyridines with a chain length of up to eight carbon atoms have been described in U.S. Pat. No. 5,298,486 and EP 0 470 391 and in *Perfumer & Flavorist,* 1994, Vol. 19, March/April 19-27: thus the sensorial profile of 3-n-octyl pyridine has been described as "fruity, juicy, seafood".

4-heptyl pyridine has been isolated as a component in orange oil (*J. Agric. Food Chem.* 1992, 40, 2236-2243), but nothing is said there about its olfactory characteristics.

In *Annales de Chimie,* 1944, 19, 487-521 on page 509 it is commented that starting with 4-tridecyl pyridine all higher homologues of 4-n-alkyl pyridine have a "pleasant odor".

4-n-tetradecyl pyridine, 4-n-hexadecyl pyridine and 4-n-octadecyl pyridine are described in *Eur. J. Org. Chem.* 2004, 835-849 as "very unpleasant smelling" substances.

In summary, it can be said that the olfactory characteristics of 4-$C_8$-$C_{12}$-alkyl pyridines, in particular the 4-n-$C_8$-$C_{12}$-alkyl pyridines, particularly the 4-$C_{10}$-alkyl pyridines, and here in turn especially 4-n-decyl pyridine, and the use and effects of these in odiferous substance mixtures have thus far been unknown.

Surprisingly, it now transpires that the 4-$C_8$-$C_{12}$-alkyl pyridines, here in particular the 4-n-$C_8$-$C_{12}$-alkyl pyridines, to be used according to the invention, have a very distinct olfactory profile, which is notably different from 7-methyl-2H-1,5-benzodioxepin-3(4H)-one (Calone 1951®) and 4-(4,8-dimethyl-3,7-nonadienyl)-pyridine (Maritima®).

The 4-$C_8$-$C_{12}$-alkyl pyridines to be used according to the invention, here in particular the 4-n-$C_8$-$C_{12}$-alkyl pyridines, according to the chain length, have a superior intensity and diffusivity ("olfactory perception across the room"), which in combination with the olfactory characteristics is completely unique.

The olfactory descriptions of the individual compounds are as follows:

4-n-octyl pyridine very intensive marine (watery) odor with an ozone note. Slightly butyrate aspects and the impression of seaweed. The ozone notes in particular, in combination with the aldehyde and ozone characteristics also remain dominant in the after-odor.

4-n-nonyl pyridine distinctive odor of the sea; in all phases of the scent process, strong, impressive marine (watery) note, which alters its character very little. Reminiscent of the odor of algae, slight hazelnut aspects. Enormously powerful and diffusive.

4-n-decyl pyridine of all the substances described here, 4-n-decyl pyridine is the strongest fragrance. It is characterised in particular by the valuable marine character prized and sought after by perfumists, which as the heart note dominates the focal point of the scent development. Further accompanying notes such as ozone, buttery diacetyl aspects and echoes of orange peel can be recorded.

4-n-undecyl pyridine marine character, combining an aldehyde-like note with slight echoes of mandarin. Very intensively watery and linear. Marine-floral scent with hints of ozone and fatty aldehydes.

4-n-dodecyl pyridine

Marine (watery) note, reminiscent of seaweed. Fresh, ozone-like, but not as intensive as, for example, 4-n-decyl pyridine. Citric aspects are combined with a nutty-dusty note.

In mixtures with other odiferous substances 4-n-alkyl pyridines and in particular the 4-n-decyl pyridine according to the invention are also able in small doses to strengthen the intensity of an odiferous substance mixture and to round off the general olfactory perception of the odiferous substance mixture and lend the mixture greater radiance and freshness as well as naturalness.

In summary therefore the following compounds and mixtures according to the invention have a surprising olfactory quality:

- odiferous or aromatic substance mixtures containing one or more 4-$C_8$-$C_{12}$-alkyl pyridine(s), preferably 4-n-$C_8$-$C_{12}$-alkyl pyridines;
- odiferous or aromatic substance mixtures containing one or more 4-$C_8$-$C_{12}$-alkyl pyridine(s), preferably 4-n-$C_8$-$C_{12}$-alkyl pyridines, and one or more further odiferous or aromatic substance(s).

An aspect of the invention closely related to that discussed above concerns the use of 4-$C_8$-$C_{12}$-alkyl pyridines, preferably 4-n-$C_8$-$C_{12}$-alkyl pyridines, or an odiferous or aromatic substance mixture (as characterised above) containing 4-$C_8$-$C_{12}$-alkyl pyridines, preferably 4-n-$C_8$-$C_{12}$-alkyl pyridines, as a marine odiferous or aromatic substance or as a marine odiferous or aromatic substance mixture.

In a corresponding method according to the invention to convey, intensify or modify a marine odor, a sensorially active quantity of 4-$C_8$-$C_{12}$-alkyl pyridines, preferably 4-n-$C_8$-$C_{12}$-alkyl pyridines, or an odiferous or aromatic substance mixture containing 4-$C_8$-$C_{12}$-alkyl pyridines, preferably 4-n-$C_8$-$C_{12}$-alkyl pyridines, is brought into contact or mixed with a product.

According to the invention, therefore, aromatic substance mixtures and odiferous substance mixtures (perfume oils) are provided, which contain one or more 4-$C_8$-$C_{12}$-alkyl pyridine(s) and one or more further odiferous or aromatic substance(s). Here the 4-$C_8$-$C_{12}$-alkyl pyridines are preferably 4-n-$C_8$-$C_{12}$-alkyl pyridines. Particular preference is for the 4-$C_8$-$C_{12}$-alkyl pyridines selected from the group comprising 4-n-octyl pyridine, 4-n-nonyl pyridine, 4-n-decyl pyridine, 4-n-undecyl pyridine, 4-n-dodecyl pyridine and mixtures of one or more of these substances. Particular preference as 4-$C_8$-$C_{12}$-alkyl pyridines are mixtures containing 4-n-decyl pyridine on its own or with one or more further 4-$C_8$-$C_{12}$-alkyl pyridine(s), preferably one or more further 4-n-$C_8$-$C_{12}$-alkyl pyridine(s). The aromatic and odiferous substance mixtures according to the invention allow the abovementioned advantages to be achieved and in particular mixtures with a valuable marine odor or watery character to be provided.

The 4-$C_8$-$C_{12}$-alkyl pyridines also bring about their advantageous effects in products containing these substances. According to the invention, therefore, aromatized or perfumed products are also provided, containing an aromatic or odiferous substance mixture (perfume oil) according to the invention, as described above. Expediently here at least one of the 4-$C_8$-$C_{12}$-alkyl pyridines is present in a sensorially sufficient quantity to generate the inventively advantageous olfactory impression of the respective substance. In particular, it is expedient if the one or more 4-$C_8$-$C_{12}$-alkyl pyridine(s) is (are) present in a sufficient quantity to bring about a watery odor.

A sensorially sufficient quantity to bring about an olfactory impression can easily be determined by a person skilled in the art in view of the other components of the product by a panel of eight testers free from anosmia in relation to the respective 4-$C_8$-$C_{12}$-alkyl pyridine, in which a corresponding specimen of the product with differing concentrations of 4-$C_8$-$C_{12}$-alkyl pyridines is tested three times by each member of the panel at ambient temperature for the presence of the desired sensorial characteristic in each case. The minimum concentration is arrived at when at least four members of the panel testify to the presence of the desired sensorial characteristic. Such panel tests will be familiar to perfumists and flavorists and are used in a routine and standard way.

The product to be provided according to the invention (in particular a perfumed product according to the invention) preferably contains at least one 4-n-$C_8$-$C_{12}$-alkyl pyridine and particularly preferably 4-n-decyl pyridine on its own or together with one or more further 4-$C_8$-$C_{12}$-alkyl pyridine(s), in particular 4-n-$C_8$-$C_{12}$-alkyl pyridines. Preferred concentrations and further odiferous substances are described in yet more detail below.

U.S. Pat. No. 3,171,839 describes the production of a number of 4-alkyl pyridines (expressly 4-$C_{10}$- and 4-$C_{11}$-alkyl pyridine) from 4-picoline (4-methylpyridine) and the hydrogenation of these 4-alkyl pyridines in ethanol to form the corresponding 4-alkyl piperidines. Such synthetic mixtures are not aromatic or odiferous substance mixtures in the sense of the present invention.

Aromatic or odiferous substance mixtures according to the invention containing (i) the 4-$C_8$-$C_{12}$-alkyl pyridines to be used according to the invention and (ii) 4-picoline are not preferred.

Aromatic or odiferous substance mixtures according to the invention containing (i) the 4-$C_8$-$C_{12}$-alkyl pyridines to be used according to the invention and (ii) the 4-alkyl piperidines obtainable by means of hydrogenation are likewise not preferred.

The theory according to the invention also covers the use of one or more 4-$C_8$-$C_{12}$-alkyl pyridine(s), in particular one or more 4-n-$C_8$-$C_{12}$-alkyl pyridines to convey, intensify or modify a marine odor;

strengthen the intensity of an odiferous substance mixture;

convey, modify or intensify the radiance, freshness and/or naturalness of an odiferous substance mixture;

round off the odor of an odiferous substance mixture;

intensify and/or modify an odor or taste, and/or increase the substantivity or diffusivity of an odiferous substance or an odiferous substance mixture.

Particularly preferred for the stated purposes is 4-n-decyl pyridine and the aromatic and odiferous substance mixtures according to the invention described above containing 4-n-decyl pyridine.

Accordingly a method is also indicated according to the invention to convey, intensify or modify a marine odor;

strengthen the intensity of an odiferous substance mixture;

convey, modify or intensify the radiance, freshness and/or naturalness of an odiferous substance mixture;

round off the odor of an odiferous substance mixture;

intensify and/or modify an odor or taste, and/or increase the substantivity or diffusivity of an odiferous substance or an odiferous substance mixture.

comprising the bringing into contact, preferably mixing of one or more 4-$C_8$-$C_{12}$-alkyl pyridine(s), preferably 4-n-$C_8$-$C_{12}$-alkyl pyridines, in a sensorially active quantity with a product.

Odiferous and aromatic substance compositions according to the invention, in particular perfume oils, contain preferably two, three, four, five, six, seven, eight, nine, ten or more odiferous substances, preferably selected from the substances mentioned below:

General substances as mentioned in Steffen Arctander, Perfume and Flavor Chemicals, published by the author, Montclair, N.J. 1969; H. Surburg, J. Panten, Common Fragrance and Flavor Materials, 5th Edition, Wiley-VCH, Weinheim 2006.

Odiferous substances that can be combined with 4-$C_8$-$C_{12}$-alkyl pyridines and in particular 4-n-$C_8$-$C_{12}$-alkyl pyridines are as follows:

extracts from natural raw materials such as essential oils, concretes, absolutes, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; estragon oil; eucalyptus citriodora oil; eucalyptus oil; fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

individual fragrances from the group comprising hydrocarbons, such as for example 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene;

from the group comprising aliphatic alcohols, such as for example hexanol; octanol; 3-octanol; 2,6-dimethylheptanol; 2-methylheptanol, 2-methyloctanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

from the group comprising aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal-diethylacetal; 1,1-dimethoxy-2,2,5-trimethyl-4-hexene; citronellyl oxyace-aldehyde;

from the group comprising aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one;

from the group comprising aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

from the group comprising aliphatic nitriles, such as for example 2-nonenenitrile; 2-tridecenenitrile; 2,12-tridecadienenitrile; 3,7-dimethyl-2,6-octadienenitrile; 3,7-dimethyl-6-octenenitrile;

from the group comprising aliphatic carboxylic acids and esters thereof, such as for example (E)- and (Z)-3-hexenyl-formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate;

from the group comprising acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

from the group comprising acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl and diethyl acetals of geranial, neral and 7-hydroxy-3,7-dimethyloctanal;

from the group comprising cyclic terpene alcohols, such as, for example, menthol; isopulegol; alpha-terpineol; terpinen-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

from the group comprising cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; gamma-damascone; delta-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

from the group comprising cyclic alcohols, such as, for example, 4-tert.-butylcyclohexanol; 3,3,5-trimethylcyclohexanol; 3-isocamphylcyclohexanol; 2,6,9-trimethyl-(Z2,Z5,E9)-cyclododecatrien-1-ol; 2-isobutyl-4-methyltetrahydro-2H-pyran-4-ol;

from the group comprising cycloaliphatic alcohols, such as, for example, alpha,3,3-trimethylcyclo-hexyl methanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

from the group comprising cyclic and cycloaliphatic ethers, such as, for example, cineole; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methylpropyl)-1,3-dioxane;

from the group comprising cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

from the group comprising cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

from the group comprising cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl) ketone;

from the group comprising esters of cyclic alcohols, such as, for example, 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or -6-indenyl acetate; 4,7-methano-3a,4,5,6,7,7a-hexahydro-5- or -6-indenyl propionate; 4,7-methano-3a,4,5,6,7,7a-hexahydro-5- or -6-indenyl-isobutyrate; 4,7-methanooctahydro-5- or -6-indenyl acetate;

from the group comprising esters of cycloaliphatic carboxylic acids, such as, for example, allyl-3-cyclohexyl-propionate; allyl cyclohexyl oxyacetate; methyl dihydrojasmonate; methyl jasmonate; methyl-2-hexyl-3-oxycyclopentanecarboxylate; ethyl-2-ethyl-6,6-dimethyl-2-cyclohexenecarboxylate; ethyl 2,3,6,6-tetramethyl-2-cyclohexenecarboxylate; ethyl-2-methyl-1,3-dioxolane-2-acetate;

from the group comprising aromatic carbons such as for example styrene and diphenylmethane;

from the group comprising araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

from the group comprising esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

from the group comprising araliphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

from the group comprising aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butyl cinnamaldehyde; alpha-amylcinnamaldehyde; alpha-hexyl cinnamaldehyde; 3-methyl-5-phenylpentanal; 4-methoxybenz-aldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)propanal; 2-methyl-3-(4-methylendioxyphenyl)propanal;

from the group comprising aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexa-methyl-2-acetonaphthone;

from the group comprising aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethyl benzoate; ethyl-3-phenylglycidate; ethyl-3-methyl-3-phenylglycidate;

from the group comprising nitrogen-containing aromatic compounds, such as, for example, 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methyl-N-methylanthranilate; Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine; 4-(4,8-dimethyl-3,7-nonadienyl)-pyridine;

from the group comprising phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

from the group comprising heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

from the group comprising lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

The perfume oils containing the 4-$C_8$-$C_{12}$-alkyl pyridines to be used according to the invention, preferably 4-n-$C_8$-$C_{12}$-alkyl pyridines, can be used in liquid form, undiluted or diluted with a solvent for perfuming purposes. Suitable solvents for this are in particular ethanol, isopropanol, diethylene glycol monoethyl ether, glycerine, propylene glycol, 1,2-butylene glycol, dipropylene glycol, diethyl phthalate, triethyl citrate and isopropyl myristate. These solvents are adjuvants in perfuming and should not be seen as odiferous substances (in the sense of the invention).

Mixtures or solutions of certain 4-alkyl pyridines are known, for example of 4-n-decyl pyridine in ethanol (Langmuir 2001, 1054-1059) or methanol (U.S. Pat. No. 4,555,520 and Journal of Solid State Chemistry 1987, 69, 145-152).

If these solvents, in particular ethanol or methanol, are nevertheless seen as aromatic and/or odiferous substances, an aromatic and/or odiferous substance mixture according to the invention contains in addition to these solvents one or more 4-$C_8$-$C_{12}$-alkyl pyridine(s) plus one or more further odiferous or aromatic substance(s).

In odiferous substance and aromatic substance mixtures, in particular in perfume oil compositions, the total quantity used of 4-$C_8$-$C_{12}$-alkyl pyridines, preferably of 4-n-$C_8$-$C_{12}$-alkyl pyridines, is normally in the range 0.000001 to 5 Wt %, preferably 0.00001 to 2 Wt % and particularly preferably 0.0001 to 1 Wt %, in each case with reference to the odiferous substance- or aromatic substance mixture as a whole.

In small doses according to a further aspect of the invention it was found that the 4-$C_8$-$C_{12}$-alkyl pyridines to be used according to the invention, in particular the 4-n-$C_8$-$C_{12}$-alkyl pyridines, are particularly suited, in the low concentrations mentioned in the following, for modifying and/or intensifying an odor or taste, i.e. that they are able to function as so-called boosters or enhancers.

Where the 4-$C_8$-$C_{12}$-alkyl pyridines to be used according to the invention, in particular the 4-n-$C_8$-$C_{12}$-alkyl pyridines, are mainly used in order to lend an odiferous substance mixture and aromatic substance mixture, in particular a perfume oil composition, greater intensity, freshness, radiance and/or rounding and/or to intensify certain notes (other odiferous or aromatic substances contained in the odiferous substance and aromatic substance mixture), in particular notes in the flowery, fruity, marine or mossy directions, the total proportion of 4-n-$C_8$-$C_{12}$-alkyl pyridines is preferably quite low and is preferably in the range 0.00001 to 1 Wt %, preferably in the range 0.0001 to 0.1 Wt % and particularly preferably in the range 0.001 to 0.01 Wt %, in each case with reference to the total quantity of odiferous substance or aromatic substance mixture.

Where within the preferred concentration ranges a comparatively low concentration is selected, depending on the further components in the respective composition, in some cases the characteristic fragrance notes mentioned above are still not conveyed.

In view of this aspect of the present invention it has already been stated that the 4-$C_8$-$C_{12}$-alkyl pyridines to be used according to the invention, in particular the 4-n-$C_8$-$C_{12}$-alkyl pyridines, can be used as boosters for odiferous or aromatic substances. A corresponding method to modify and/or intensify (boost) an odor and/or taste with one, a plurality or all of the flowery, fruity, marine and/or mossy notes, comprises the following step:

mixing one or more odiferous or aromatic substance(s) with one, a plurality or all of the flowery, fruity, marine and/or mossy notes, with a quantity of 4-$C_8$-$C_{12}$-alkyl pyridines, in particular the 4-n-$C_8$-$C_{12}$-alkyl pyridines, sufficient to sensorially modify and/or enhance the olfactory and/or flavor impression of the odiferous or aromatic substance(s) generating one or more of the flowery, fruity, marine and/or mossy notes.

With other marine odiferous substances, by mixing with the 4-$C_8$-$C_{12}$-alkyl pyridines to be used according to the invention, preferably 4-n-$C_8$-$C_{12}$-alkyl pyridines, further combinations and effects of olfactory interest can be obtained, in particular in combination with Calone 1951® or Maritima® multifaceted sea notes can be achieved.

The olfactory intensification of flowery odiferous or aromatic substances by the 4-$C_8$-$C_{12}$-alkyl pyridines to be used according to the invention, in particular the 4-n-$C_8$-$C_{12}$-alkyl pyridines, is observed in particular in odiferous or aromatic substances with a flowery odor or taste in the directions of jasmine, rose, lily of the valley, violet, geranium, magnolia, iris, narcissus, freesia, boronia, tuberose, Cape jasmine and hyacinth.

Flowery odiferous or aromatic substances, with which the 4-$C_8$-$C_{12}$-alkyl pyridines to be used according to the invention, in particular the 4-n-$C_8$-$C_{12}$-alkyl pyridines, can be advantageously combined, are preferably selected from the group comprising: hydroxycitronellal, methoxycitronellal, cyclamen aldehyde [2-Methyl-3-(4-isopropylphenyl)propanal], 1-(4-isopropyl-cyclohexyl)ethanol (Mugetanol®), 4-tert-butyl-α-methyl dihydrocinnamaldehyde (Lilial®), cishexahydrocuminyl alcohol (Mayol®), 3-[4-(1,1-dimethylethyl)phenyl]propanal (Bourgeonal®), 2,2-dimethyl-3-(3-methylphenyl)propanol (Majantol®), 3-methyl-3-(3-methylbenzyl)-butan-2-ol, 2-isobutyl-4-methyltetrahydro-2H-pyran-4-ol (Florosa®), 2-methyl-3-(3,4-methylenedioxyphenyl)propanal (Heliofolal®), 4-(4-hydroxy-4-methylpentyl)-3-cyclohexene carbaldehyde (Lyral®), 4-(octahydro-4,7-methano-5H-inden-5-ylidene-butanal (Dupical®), vernaldehyde, 4-(4-methyl-3-penten-1-yl)-3-cyclohexene carbaldehyde (Vertomugal®), octahydro-5-(4-methoxybutylidene)-4,7-methano-1H-indene (Mugoflor®), 2,6-dimethyl-2-heptanol (Freesiol®), 1-ethyl-1-methyl-3-phenylpropanol (Phemec®), 2,2-Dimethyl-3-phenyl-1-propanol (Muguet alcohol), profarnesol, dihydrofarnesol, farnesol, neriolidol, hydroxycitronellal dimethyl acetal, hexyl benzoate, geraniol, nerol, linalool, tetrahydrogeraniol, tetrahydrolinalool, ethyl linalool, geranyl tiglinate, phenylethyl alcohol (2-phenylethyl alcohol), citronellol, rose oxide, 2-methyl-5-phenylpentanol (Rosaphen), 3-methyl-5-phenylpentanol (Phenoxanol), methyl dihydrojasmonate (Hedion®, Hedione® high cis), 2-heptyl cyclopentanone (Projasmon P), cis-jasmone, dihydrojasmonate, cinnamic alcohol (3-phenyl-2-propen-1-ol), dihydrocinnamic alcohol (3-phenylpropanol), 2-methyl-4-phenyl-1,3-dioxolane (Jacinthaflor®), dihydromyrcenol (2,6-dimethyl-7-octen-2-ol).

The olfactory intensification of fruity odiferous or aromatic substances by the 4-$C_8$-$C_{12}$-alkyl pyridines to be used according to the invention, in particular the 4-n-$C_8$-$C_{12}$-alkyl pyridines, is in particular observed in odiferous or aromatic substances with a fruity odor or taste in the directions of apple, pineapples, raspberries, strawberries, bananas, blueberries, pears, grapefruit, melons, apricots, cherries, vanilla, orange, lemon, bergamot, lime, caramel and coconut.

Fruity odiferous or aromatic substances, with which the 4-$C_8$-$C_{12}$-alkyl pyridines to be used according to the invention, in particular the 4-n-$C_8$-$C_{12}$-alkyl pyridines, can advantageously be combined are preferably selected from the group comprising: 2-methyl-butyric acid ethyl ester, 4-(p-hydroxyphenyl)-2-butanone, ethyl-3-methyl-3-phenyl glycidate, butyric acid isoamyl ester, acetic acid isoamyl ester, acetic acid-n-butyl ester, butyric acid ethyl ester, 3-methyl-butyric acid ethyl ester, n-hexanoic acid ethyl ester, n-hexanoic acid allyl ester, ethyl-2-trans-4-cis-decadienoate, 1,1-dimethoxy-2,2,5-trimethyl-4-hexane, 2,6-dimethyl-5-hepten-1-al, gamma-undecalactone, gamma-nonalactone, hexanal, 3Z-hexenal, n-decanal, n-dodecanal, citral, limonene, vanillin, ethyl vanillin, maltol, ethyl maltol and mixtures thereof.

For some applications it is advantageous to use the perfume oils containing 4-$C_8$-$C_{12}$-alkyl pyridines, preferably 4-n-$C_8$-$C_{12}$-alkyl pyridines, adsorbed on a carrier, which ensures both a fine distribution of the odiferous substances in the product and a controlled release in use. Such carriers can be porous inorganic materials such as light sulfate, silica gel, zeolites, gypsum, clays, clay granulates, gas concrete and so on or organic materials such as woods, cellulose-based materials, sugar or plastics such as PVC, polyvinyl acetate or polyurethane.

For other applications it is advantageous for the perfume oils containing 4-$C_8$-$C_{12}$-alkyl pyridines, preferably 4-n-$C_8$-$C_{12}$-alkyl pyridines, to be used in microencapsulated, spray-dried form as an inclusion complex or extrusion product and added in this form to the (primary) product to be perfumed.

The characteristics of such modified perfume oils are in some cases further optimized by so-called coating with suitable materials with a view to a more directed scent release, for which preferably waxy synthetic materials such as polyvinyl alcohol are used.

Microencapsulation of the perfume oils can take place, for example, using the so-called coacervation process with the help of capsule materials in, for example, polyurethane-like materials or soft gelatine. Spray-dried perfume oils can, for example, be produced by spray-drying an emulsion or dispersion containing the perfume oil, wherein as the carrier material modified starches, proteins, dextrin and vegetable gums can be used. Inclusion complexes can, for example, be produced by introducing dispersions of the perfume oil and cyclodextrins or urea derivatives into a suitable solvent, e.g. water. Extrusion products can be obtained by melting the perfume oils with a suitable waxy substance and by extrusion followed by solidification, if necessary in a suitable solvent such as isopropanol.

The perfume oils containing 4-$C_8$-$C_{12}$-alkyl pyridines, preferably 4-n-$C_8$-$C_{12}$-alkyl pyridines, according to the invention, can be used in concentrated form, in solutions or in another modified form for the production of for example perfume extracts, eau de perfumes, eau de toilettes, after-shaves, eau de colognes, pre-shave products, splash colognes and perfumed freshening wipes and for perfuming acid, alkaline and neutral cleaning agents such as, for example, floor cleaners, window cleaners, washing-up liquids, bath and sanitary equipment cleaners, scouring agents, solid and liquid WC cleaners, carpet cleaners in powder and foam form, liquid detergents, powder detergents, laundry pre-treatment agents such as bleaching agents, softeners and stain removers, fabric conditioners, laundry soaps, laundry tablets, disinfectants, surface disinfectants and air fresheners in liquid or gel form or applied to a solid support, aerosol sprays, waxes and polishes such as furniture polishes, floor waxes, cream shoe polishes and personal hygiene agents such as, for example, solid and liquid soaps, shower gels, shampoos, shaving soaps, shaving foams, bath oils, cosmetic emulsions of the oil-in-water, of the water-in-oil and of the water-in-oil-in-water type such as, for example, skin creams and lotions, face creams and lotions, sun protection creams and lotions, after-sun creams and lotions, hand creams and lotions, foot creams and lotions, depilatory creams and lotions, after-shave creams and lotions, bronzing creams and lotions, hair care products such as, for example, hair sprays, hair gels, hair lotions, hair rinses, permanent and semi-permanent hair dyes, hair shaping agents such as cold permanent waves and hair smoothing agents, hair tonics, hair creams and lotions, deodorants and antiperspirants such as, for example, under-arm sprays, roll-ons, deodorant sticks, deodorant creams or decorative cosmetic products.

The abovementioned perfumed products preferably have a content of perfume oils according to the invention, containing the 4-$C_8$-$C_{12}$-alkyl pyridines to be used according to the invention, preferably the 4-n-$C_8$-$C_{12}$-alkyl pyridines, in the range 0.1 to 6 Wt %, preferably in the range 0.2 to 4 Wt %, preferably in the range 0.3 to 3 Wt %, in each case with reference to the total weight of the perfumed product.

Preferred substances, with which the 4-$C_8$-$C_{12}$-alkyl pyridines to be used according to the invention, preferably the 4-n-$C_8$-$C_{12}$-alkyl pyridines, or the odiferous or aromatic substance mixtures according to the invention can be combined are:

preservatives, abrasives, antiacne agents, agents against ageing of the skin, antibacterial agents, anticellulitis agents, antidandruff agents, antiinflammatory agents, irritation-preventing agents, irritation-inhibiting agents, antimicrobial agents, antioxidants, astringents, perspiration-inhibiting agents, antiseptic agents, antistatics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, fungicides, gelling agents, gel-forming agents, hair care agents, hair setting agents, hair straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin soothing agents, skin cleansing agents, skin care agents, skin healing agents, skin lightening agents, skin protecting agents, skin softening agents, cooling agents, skin cooling agents, warming agents, skin warming agents, stabilizers, UV-absorbing agents, UV filters, detergents, fabric conditioners, suspending agents, skin tanning agents, thickeners, vitamins, oils, waxes, fats, phospholipids, saturated fatty acids, mono- or polyunsaturated fatty acids, $\alpha$-hydroxy acids, polyhydroxy-fatty acids, liquefiers, dyestuffs, colour-protecting agents, pigments, anticorrosives, aromas, flavoring substances, odoriferous substances, polyols, surfactants, electrolytes, organic solvents or silicone derivatives.

The 4-$C_8$-$C_{12}$-alkyl pyridines, preferably the 4-n-$C_8$-$C_{12}$-alkyl pyridines, are furthermore characterised by a high (inherent) bonding, a very low olfactory threshold, a high diffusivity, good substantivity and very good fixation characteristics. Compared with Calone 1951® or Maritima® the 4-$C_8$-$C_{12}$-alkyl pyridines to be used according to the invention, particularly the 4-n-$C_8$-$C_{12}$-alkyl pyridines, have a good stability with regard to oxidative reagents (such as for example in bleaching solutions) and an extremely low threshold value and extraordinary diffusivity. The 4-$C_8$-$C_{12}$-alkyl pyridines, in particular the 4-n-$C_8$-$C_{12}$-alkyl pyridines, here in particular 4-n-decyl pyridine, are therefore particularly suited to use in air-fresheners, shampoos, bleaching agents and detergents and fabric conditioners.

In order to illustrate the characteristics described above, in the following way the diffusivity and threshold value in air of Maritima® and 4-decyl pyridine were compared:

Example of Diffusivity:

0.5 g of the odiferous substances to be tested are each weighed in a Petri dish and sealed with the lid. The Petri dish is placed 50 cm in front of the test subject (the distance is marked on the table before the test commences).

The lid is then removed from the Petri dish and a stopwatch is simultaneously started by the test subject. The test subject stops the time immediately he perceives the odor. The test subject assesses the intensity of the sample on a scale of 1=odorless to 9=very strong. The stop time and the intensity are noted on the test sheet.

Each sample is evaluated by the test subject three times. In order to be certain that the result is not distorted, all windows and doors must be shut. The room is at normal temperature (20-25° C.). The test subjects do not suffer from anosmia in respect of the samples to be tested. As a rule a minimum of 8 participants evaluate the sample.

| Test | Scale | 4-decyl pyridine | Maritima ® |
|---|---|---|---|
| Diffusivity | 1-9 | 8.1 | 3.4 |

Example of the Threshold Value in Air:

The odiferous substance to be tested is evaporated in a defined sampling system and then assessed sensorially with regard to the perception threshold. The sampling system comprises the sample bag and a gas stream outlet. A defined quantity of the desired odiferous substance is squirted into the bag. The equilibrium time after filling with the sample is approximately 18 hours at ambient temperature; then the content of the bag is presented to the test subject by means of a constant gas stream. At the first discernable olfactory impression a response button is pressed. The odor threshold concentration is achieved when in the next dilution stage the olfactory impression is confirmed by repeated pressing of the response button. The concentration of the sample is increased between the previous and the next samples by a factor of 2.

The assessment of the threshold value in air is measured against a standard and as a rule 8 test subjects take part in the sensorial evaluation. The participants have no anosmia in respect of the samples to be investigated.

| Test | Scale | 4-decyl pyridine | Maritima ® |
|---|---|---|---|
| Threshold value in air | [ppm] | 0.014 | 0.155 |

The (inherent) bonding, also referred to as the attachment capacity, refers to the capacity of a compound to bond to a substrate. Diffusivity means the speed at which the transmission of the odiferous substances through the room is perceived. Substantivity means the capacity to be absorbed from a usually aqueous phase by a substrate or also following a washing or rinsing process to remain on a substrate. This effect manifests itself in particular on substrates such as skin, hair and textile fibres (e.g. cotton, wool, linen, synthetic fibres). The feature of being able to work as a fixator (fixation characteristic) means that the corresponding compound generates adhesive strength in other odiferous substances. This can take place, for example, by vapor pressure depression or olfactory intensification (e.g. lowering the threshold value).

The described effects of the 4-$C_8$-$C_{12}$-alkyl pyridines, preferably the 4-n-$C_8$-$C_{12}$-alkyl pyridines, and the mixtures according to the invention on odiferous substance compositions are particularly evident in a comparison of the olfactory change over time in use.

The following examples explain the invention. Unless otherwise stated all data, in particular quantities and percentages, relate to the weight.

The following abbreviations are used: BA=benzyl alcohol, BB=benzyl benzoate; DEP=diethyl phthalate; DPG=dipropylene glycol, IPM=isopropyl myristate, CRIST.=crystalline, TEC=triethyl citrate

EXAMPLES

Example 1

Production of Various 4-n-alkyl Pyridines Using the Example of 4-n-decyl Pyridine 160 g of 4-picoline are droppered into a solution of 1,000 ml lithium diisopropylamide (1.8 M) in 1,600 ml tetrahydrofuran at −50° C. and within 20 minutes. Then the formulation is stirred for one hour at −20° C. A solution of 330 g of nonyl bromide in 400 ml of tetrahydrofuran is droppered in within two hours at −50° C., further stirred for an hour and the formulation then left to revert to room temperature. 600 ml of water are added, the phases separated and the organic phase distilled.

181 g of 4-n-decyl pyridine with a purity of 99.3% are isolated. This corresponds to a theoretical yield of 51%.

4-octyl pyridine

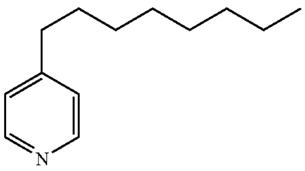

$^1$H-NMR (400 MHz, $CDCl_3$): δ=0.88 (t, J=6.9 Hz, 3H), 1.22-1.36 (m, 10H), 1.57-1.67 (m, 2H), 2.59 (m, 2H), 7.10 (m, 2H), 8.48 (dd, J=1.6 Hz, J=4.4 Hz, 2H) ppm.

$^{13}$C-NMR (100 MHz, $CDCl_3$): δ=14.09 ($CH_3$), 22.65 ($CH_2$), 29.19 (2×$CH_2$), 29.37 ($CH_2$), 30.31 ($CH_2$), 31.84 ($CH_2$), 35.26 ($CH_2$), 123.91 (2×CH), 149.62 (2×CH), 151.77 (C) ppm.

MS: m/z (%)=191 (8) [$M^+$], 162 (4), 148 (6), 134 (4), 120 (6), 106 (82), 93 (100), 65 (9).

4-nonyl pyridine

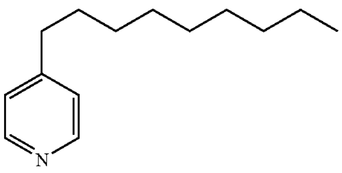

$^1$H-NMR (400 MHz, $CDCl_3$): δ=0.88 (t, J=6.8 Hz, 3H), 1.21-1.36 (m, 12H), 1.56-1.68 (m, 2H), 2.59 (m, 2H), 7.10 (m, 2H), 8.48 (dd, J=4.4 Hz, J=1.6 Hz, 2H) ppm.

$^{13}$C-NMR (100 MHz, $CDCl_3$): δ=14.11 ($CH_3$), 22.67 ($CH_2$), 29.19 ($CH_2$), 29.29 ($CH_2$), 29.41 ($CH_2$), 29.49 ($CH_2$), 30.32 ($CH_2$), 31.88 ($CH_2$), 35.26 ($CH_2$), 123.92 (2×CH), 149.62 (2×CH), 151.78 (C) ppm.

MS: m/z (%)=205 (8) [$M^+$], 190 (2), 176 (3), 162 (7), 148 (4), 134 (2), 120 (6), 106 (100), 93 (65), 65 (7).

4-decyl pyridine

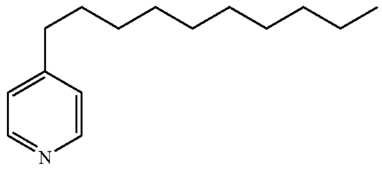 [SMILES: CCCCCCCCCCc1ccncc1]

$^1$H-NMR (400 MHz, $CDCl_3$): δ=0.88 (t, J=6.8 Hz, 3H), 1.22-1.35 (m, 14H), 1.57-1.67 (m, 2H), 2.59 (m, 2H), 7.10 (m, 2H), 8.47 (dd, J=4.4 Hz, J=1.6 Hz, 2H) ppm.

$^{13}$C-NMR (100 MHz, $CDCl_3$): δ=14.11 ($CH_3$), 22.69 ($CH_2$), 29.19 ($CH_2$), 29.31 ($CH_2$), 29.41 ($CH_2$), 29.53 ($CH_2$), 29.58 ($CH_2$), 30.31 ($CH_2$), 31.90 ($CH_2$), 35.26 ($CH_2$), 123.92 (2×CH), 149.61 (2×CH), 151.79 (C) ppm.

MS: m/z (%)=219 (6) [$M^+$], 204 (4), 190 (5), 176 (7), 162 (7), 148 (5), 134 (2), 120 (8), 106 (100), 93 (47), 77 (3).

4-undecyl pyridine

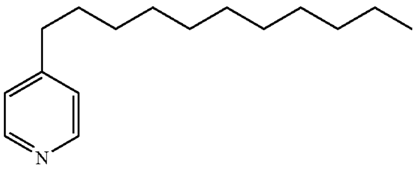 [SMILES: CCCCCCCCCCCc1ccncc1]

$^1$H-NMR (400 MHz, $CDCl_3$): δ=0.88 (t, J=6.7 Hz, 3H), 1.22-1.35 (m, 16H), 1.57-1.66 (m, 2H), 2.59 (m, 2H), 7.10 (m, 2H), 8.47 (dd, J=1.6 Hz, J=6.0 Hz, 2H) ppm.

$^{13}$C-NMR (100 MHz, $CDCl_3$): δ=14.12 ($CH_3$), 22.70 ($CH_2$), 29.20 ($CH_2$), 29.34 ($CH_2$), 29.41 ($CH_2$), 29.53 ($CH_2$), 29.62 ($CH_2$), 29.63 ($CH_2$), 30.31 ($CH_2$), 31.92 ($CH_2$), 35.26 ($CH_2$), 123.92 (2×CH), 149.62 (2×CH), 151.78 (C) ppm.

MS: m/z (%)=233 (11) [$M^+$], 218 (4), 204 (5), 190 (6), 176 (3), 162 (6), 148 (4), 134 (2), 120 (6), 106 (100), 93 (41), 65 (5).

Example 2

Perfume Oil Compositions and Formulation Examples

Example 2.1

Washing Powder

| Material | Producer | Chemical name | Function | Wt % |
|---|---|---|---|---|
| Sodium metasilicate pentahydrate | Akzo Nobel Chemicals, Germany | Sodium metasilicate pentahydrate | | 48.0 |
| Sodium hydrogen carbonate | Various | Sodium hydrogen carbonate | Alkali | 15.0 |
| Sodium percarbonate | Various | Sodium carbonate peroxyhydrate | Bleaching agent | 15.0 |

-continued

| Material | Producer | Chemical name | Function | Wt % |
|---|---|---|---|---|
| Peractive AC Blue | Clariant GmbH, Germany | TAED/Na-carboxy-methylcellulose | Activator | 5.00 |
| Genapol OA-080 | Clariant GmbH, Germany | Oxo-alcohol C14-15,8EO | Nonionic surfactant | 3.00 |
| Texapon K12 powder | Cognis Deutschland GmbH | Sodium lauryl sulfate C12 | Anionic surfactant | 7.00 |
| Tinopal CBS-X | Ciba, Germany | | Brightener | 0.50 |
| Savinase 6.0 T, Type W | Novozymes | Protease | Enzyme | 0.40 |
| Termamyl 120 T | Novozymes | Alpha-amylase | Enzyme | 0.30 |
| Sodium sulfate | Various | Sodium sulfate | Filler | 5.50 |
| Perfume oil P1 or P2 | Symrise | | Perfume (fragrance) | 0.30 |

Perfume Oils for this Washing Powder:

| Odiferous substance(s) | Perfume oil P1 | Perfume oil P2 |
|---|---|---|
| ROSEMARY OIL | 5.0 | 5.0 |
| DIHYDROMYRCENOL | 140.0 | 140.0 |
| HERBAFLORAT (ACETIC ACID TRICYCLO[5.2.1.0]-4-DECEN-8-YLESTER) | 50.0 | 50.0 |
| ALPHA-HEXYL CINNAMALDEHYDE | 125.0 | 125.0 |
| COUMARIN | 10.0 | 10.0 |
| DIPHENYL OXIDE | 5.0 | 5.0 |
| LILIAL ® (2-METHYL-3-(4-TERT.-BUTYLPHENYL)-PROPANAL) | 40.00 | 40.00 |
| GALAXOLIDE ® 50% in DEP (1,1,2,3,3,8-hexamethyl-1,2,3,5,7,8-hexa-hydro-6-oxa-cyclopenta[b]naphthalene) | 150.0 | 150.0 |
| ISORALDEINE ® 70 ((E)-3-methyl-4-(2,6,6-trimethyl-cyclohex-2-enyl)-but-3-en-2-one) | 30.0 | 30.0 |
| ALLYL AMYL GLYCOLATE | 7.0 | 7.0 |
| ISO E SUPER ® (3-ACETYL-3,4,10,10-TETRAMETHYL-1(6)-BICYCLO[4.4.0]DECENE) | 80.0 | 80.0 |
| ROSE BASE | 100.0 | 100.0 |
| GALBANUM BASE | 15.0 | 15.0 |
| DIPROPYLENE GLYCOL (DPG) | 5.0 | 4.9 |
| APPLE BASE | 25.0 | 25.0 |
| OZONIL 10% in DPG (1Z-DODECENYL CYANIDE) | 15.0 | 15.0 |
| MELONAL ® 10% in DPG (2,6-DIMETHYL-5-HEPTENAL) | 3.0 | 3.0 |
| METHYLOCTIN CARBONATE 10% in DPG | 5.0 | 5.0 |
| DELTA-DAMASCONE 10% in DPG (1-(2,6,6-trimethyl-cyclohex-3-enyl)-but-2-en-1-one) | 7.0 | 7.0 |
| SANDRANOL ® (2-ETHYL-4-(2,2,3-TRIMETHYL-3-CYCLOPENTENYL)-2E-BUTENOL) | 20.0 | 20.0 |
| VERTOCITRAL (TRANS-2,4-DIMETHYL-1-FORMYL-3-CYCLOHEXENE) | 3.0 | 3.0 |
| AGRUMEX (ACETIC ACID-2-TERT.-BUTYL CYCLOHEXYL ESTER) | 100.0 | 100.0 |
| BENZYL ACETONE | 10.0 | 10.0 |
| ALDEHYDE C12 MNA (methyl nonyl acetaldehyde) | 5.0 | 5.0 |
| PROJASMON P (2-HEPTYL CYCLOPENTANONE) | 10.0 | 10.0 |

-continued

| Odiferous substance(s) | Perfume oil P1 | Perfume oil P2 |
|---|---|---|
| NEROLIN YARA YARA | 15.0 | 15.0 |
| INTRELEVEN ALDEHYDE 10% in DPG (10-undecenal) | 5.0 | 5.0 |
| PATCHOULI OIL | 15.0 | 15.0 |
| 4-n-DECYL PYRIDINE | | 0.1 |
| | 1,000.0 | 1,000.0 |

When 0.3% of the perfume oil P1 or P2 is dosed into a washing powder (powder detergent) the following result is obtained: the proportion of 0.01% 4-n-decyl pyridine in perfume oil P2 brings about an intensification of the lily of the valley and the fruity notes to a quite exceptional extent (booster effect). The composition with 4-n-decyl pyridine also has a fresher radiance overall.

Example 2.2

Soap

| Material | Producer | Chemical name | Function | Wt % |
|---|---|---|---|---|
| Deionized water | | Water | Solvent | 2.0 |
| Soap bases mix | Various | Sodium tallowates/ palmitates | Surfactants | 95.8 |
| Titanium dioxide | Kronos Titan GmbH, Germany | Titanium dioxide | Colorant/ Brightener | 1.0 |
| Perfume oil C1 or C2 | Symrise | | Perfume (Fragrance) | 1.20 |

Perfume Oils for this Soap

| Odiferous substance(s) | Example C1 (Comparison) | Example C2 (As per invention) |
|---|---|---|
| KETAMBER 10% in BB (Ambraketal) | 3.0 | 3.0 |
| LEMON GRASS OIL | 10.0 | 10.0 |
| ORANGE OIL TERPENE | 50.0 | 50.0 |
| ROSEMARY OIL | 1.0 | 1.0 |
| DIHYDROMYRCENOL | 65.0 | 65.0 |
| ALDEHYDE C11 (N-UNDECANAL) | 10.0 | 10.0 |
| HERBAFLORAT (ACETIC ACID TRICYCLO[5.2.1.0]-4-DECEN-8-YLESTER) | 30.0 | 30.0 |
| ALDEHYDE C10 (N-DECANAL) | 5.0 | 5.0 |
| CYCLOHEXYL ETHYL ACETATE | 15.0 | 15.0 |
| MANZANATE (2-METHYL-PENTANOIC ACID ETHYL ESTER) | 5.0 | 5.0 |
| CITRONELLA OIL | 35.0 | 35.0 |
| ALDEHYDE C12 (N-DODECANAL) | 2.0 | 2.0 |
| ALPHA-HEXYL CINNAMALDEHYDE | 75.0 | 75.0 |
| DIPHENYL OXIDE | 5.0 | 5.0 |
| LILIAL ® (PROPANAL, 2-METHYL-3-(4-TERT.-BUTYLPHENYL)-) | 70.0 | 70.0 |
| PHENYLETHYL ALCOHOL | 100.0 | 100.0 |
| TONALID ® (6-ACETYL-1,1,2,4,4,7-HEXAMETHYL-TETRALIN) | 25.0 | 25.0 |
| HEDION ® (METHYL DIHYDROJASMONATE) | 100.0 | 100.0 |
| AGRUNITRIL (2,6-DIMETHYL-5-HEPTENYLCYANIDE) | 15.0 | 15.0 |

-continued

| Odiferous substance(s) | Example C1 (Comparison) | Example C2 (As per invention) |
|---|---|---|
| CIS-3-HEXENOL | 2.0 | 2.0 |
| ISO E SUPER ® (3-ACETYL-3,4,10,10-TETRAMETHYL-1(6)-BICYCLO[4.4.0]DECENE) | 75.0 | 75.0 |
| DAMASCONE DELTA ((1-(2,6,6-trimethyl-cyclohex-3-enyl)-but-2-en-1-one) | 1.0 | 1.0 |
| GALAXOLIDE ® 50% in IPM (1,1,2,3,3,8-hexamethyl-1,2,3,5,7,8-hexahydro-6-oxa-cyclopenta[b]naphthalene) | 80.0 | 80.0 |
| ESTRAGOL | 5.0 | 5.0 |
| DIPROPYLENE GLYCOL | 7.0 | 6.3 |
| APPLE BASE | 10.0 | 10.0 |
| GALBASCONE (4,4-DIMETHYL-2-(1-OXO-4-PENTENYL)-CYCLOHEXENE) | 1.0 | 1.0 |
| MANDARIL 10% in DPG (2Z,11-DODECADIENYL CYANIDE) | 3.0 | 3.0 |
| AMBROXIDE CRIST. 10% in IPM | 3.0 | 3.0 |
| ALDEHYDE C11 MOA (methyloctyl acetaldehyde) 10% in DPG | 5.0 | 5.0 |
| ETHYL METHYL BUTYRATE-2 10% in DPG | 5.0 | 5.0 |
| DAMASCENONE 10% in DPG (2-(2,6,6-TRIMETHYL-1,3-CYCLOHEXADIEN-1-YL)-2E-(BUTEN-1-ONE) | 5.0 | 5.0 |
| VERTOCITRAL (TRANS-2,4-DIMETHYL-1-FORMYL-3-CYCLOHEXENE) | 5.0 | 5.0 |
| AGRUMEX (ACETIC ACID-2-TERT.-BUTYL CYCLOHEXYL ESTER) | 40.0 | 40.0 |
| ALDEHYDE C14, SO-CALLED | 15.0 | 15.0 |
| ALLYL HEPTYLATE | 5.0 | 5.0 |
| HEXYL ACETATE | 15.0 | 15.0 |
| BENZYL ACETATE | 30.0 | 30.0 |
| ANETHOL | 2.0 | 2.0 |
| ORYCLON ® (ACETIC ACID-4-TERT.-BUTYL CYCLOHEXYL ESTER) | 65.0 | 65.0 |
| 4-n-DECYL PYRIDINE | | 0.7 |
| | 1,000.0 | 1,000.0 |

When 1.2% of the respective perfume oil C1 or C2 is dosed into soap the effect is highly conclusive: the proportion of 0.07% 4-decyl pyridine in the perfume oil C2 brings about an enormous intensification of the fresh characteristic and gives the composition overall more radiance and power. Furthermore, the base odor of the soap is masked significantly better by the perfume oil C2.

Example 2.3

All-Purpose Cleaner

| Material | Producer | Chemical name | Function | Wt % |
|---|---|---|---|---|
| Deionized water | | Water | Solvent | 59.6 |
| Mergal K9N | Troy Chemie, Seelze | 5-chloro-2-methyl-3-(2H)-isothiazolone and 2-methyl-3-(2H)-isothiazolone | Preservative | 0.1 |

-continued

| Material | Producer | Chemical name | Function | Wt % |
|---|---|---|---|---|
| Trisodium citrate dihydrate | Various | Trisodium citrate dihydrate | Chelating agent | 3.0 |
| Zetesol NL-2 | Zschimmer & Schwarz, Germany | Fatty alcohol C12-14-sulfate, sodium | Anionic surfactant | 30.0 |
| Imbentin C/125/055 | Dr. W. Kolb AG Chem. | Fatty alcohol C12-C15, 8EO | Nonionic surfactant | 5.0 |
| Ethanol 96% | Various | Ethanol | Solvent | 2.0 |
| Perfume oil A1 or A2 | Symrise | | Perfume (Fragrance) | 0.3 |

Perfume Oils for this All-Purpose Cleaner:

| Odiferous substance(s) | Perfume oil A1 (Comparison) | Perfume oil A2 (As per invention) |
|---|---|---|
| CEDAR WOOD OIL | 8.0 | 8.0 |
| AMBROCENIDE ® 10% in DPG | 1.0 | 1.0 |
| ROSEMARY OIL | 8.0 | 8.0 |
| DIHYDROMYRCENOL | 80.0 | 80.0 |
| ISOBUTYL QUINOLINE | 0.5 | 0.5 |
| AMBROXAN | 1.0 | 1.0 |
| LIGUSTRAL (TRANS-2,4-DIMETHYL-1-FORMYL-3-CYCLOHEXENE) | 2.0 | 2.0 |
| AMYL SALICYLATE N/ISO | 24.0 | 24.0 |
| CITRONELLA OIL | 8.0 | 8.0 |
| VERTOFIX (1-(3,6,8,8-tetramethyl-2,3,4,7,8,8a-hexahydro-1H-3a,7-methano-azulen-5-yl)-ethanone) | 30.0 | 30.0 |
| ALPHA-HEXYL CINNAMALDEHYDE | 50.0 | 50.0 |
| COUMARIN | 4.0 | 4.0 |
| COUMARONE (2-ACETYL-BENZOFURAN) | 0.6 | 0.6 |
| ISOBORNYL ACETATE | 30.0 | 30.0 |
| CAMPHOR | 8.0 | 8.0 |
| LILIAL ® (2-METHYL-3-(4-TERT.-BUTYL PHENYL)-PROPANAL) | 30.0 | 30.0 |
| LINALOOL | 40.0 | 40.0 |
| LINALYL ACETATE | 40.0 | 40.0 |
| TERPINEOL | 100.0 | 100.0 |
| GALAXOLIDE ® 50% in DEP (1,1,2,3,3,8-hexamethyl-1,2,3,5,7,8-hexahydro-6-oxa-cyclopenta[b]naphthalin) | 24.0 | 24.0 |
| GLOBALIDE ® (E/Z-11-PENTADECEN-1,15-OLIDE) | 5.0 | 5.0 |
| ETHYLENE BRASSYLATE (BRASSYLIC ACID ETHANEDIOL ESTER) | 24.0 | 24.0 |
| AGRUNITRIL (2,6-DIMETHYL-5-HEPTENYLCYANIDE) | 16.0 | 16.0 |
| ISORALDEINE ® 70 (E)-3-methyl-4-(2,6,6-trimethyl-cyclohex-2-enyl)-but-3-en-2-one) | 20.0 | 20.0 |
| OZONIL (1Z-DODECENYLCYANIDE) | 1.5 | 1.5 |
| ALLYL AMYL GLYCOLATE (2-METHYLBUTOXY-ACETIC ACID ALLYL ESTER) | 15.0 | 15.0 |
| DAMASCONE DELTA ((1-(2,6,6-trimethyl-cyclohex-3-enyl)-but-2-en-1-one) | 2.0 | 2.0 |
| TIMBEROL ® (2,2,6-TRIMETHYL-1-(3-HYDROXYHEXYL)-CYCLOHEXANE) | 2.0 | 2.0 |
| ESTRAGOL | 1.0 | 1.0 |
| MYSORANE ® BASE | 10.0 | 10.0 |
| DIPROPYLENE GLYCOL | 346.2 | 346.15 |
| LEMON OIL TERPENE | 20.0 | 20.0 |

-continued

| Odiferous substance(s) | Perfume oil A1 (Comparison) | Perfume oil A2 (As per invention) |
|---|---|---|
| GERANIOL | 8.0 | 8.0 |
| GERANIUM BASE | 5.0 | 5.0 |
| PATCHOULI BASE | 8.0 | 8.0 |
| GALBASCONE 10% in DPG (4,4-DIMETHYL-2-(1-OXO-4-PENTENYL)-CYCLOHEXENE) | 2.0 | 2.0 |
| CALONE ® 1951 10% in DPG (7-METHYL-3,4-DIHYDRO-3-BENZODIOXEPINONE) | 4.0 | 4.0 |
| ISOBUTYL QUINOLINE | 0.2 | 0.2 |
| EUGENOL | 1.5 | 1.5 |
| FARENAL ® (2,6,10-TRIMETHYL-9-UNDECENAL) | 0.5 | 0.5 |
| LIME OIL | 12.0 | 12.0 |
| ANETHOLE | 4.0 | 4.0 |
| BETA-METHYL NAPHTHYL KETONE | 3.0 | 3.0 |
| 4-n-DECYL PYRIDINE | | 0.05 |
| | 1,000.0 | 1,000.0 |

When 0.3% of the perfume oil is dosed into an all-purpose cleaner the following result is obtained: a proportion of 0.005% of 4-n-decyl pyridine brings about an extreme intensification of the marine-mossy note coupled with a distinct intensification of the fresh head note. The diffusivity is also increased.

Example 2.4

Shampoo

| Material | Producer | INCI name | Wt % |
|---|---|---|---|
| Deionized water | | Water | 71.5 |
| Plantacare PS 10 | Cognis Deutschland GmbH | Sodium laureth sulfate, lauryl glucoside | 20.0 |
| Euperlan PK 771 | Cognis Deutschland GmbH | Glycol distearate, sodium lauryl sulfate, cocamide MEA, Laureth-10 | 6.0 |
| Dragocid Liquid | Symrise | Phenoxyethanol, methylparaben, ethylparaben, butylparaben, propylparaben, isobutylparaben | 0.5 |
| Sodium chloride | | Sodium chloride | 1.4 |
| Citric acid monohydrate crystalline | | Citric acid | 0.1 |
| Perfume oil S1 or S2 | Symrise | Perfume (fragrance) | 0.5 |

Perfume Oils for this Pearl-Luster Shampoo:

| Odiferous substance(s) | Perfume oil A1 (Comparison) | Perfume oil A2 (As per invention) |
|---|---|---|
| CLOVE BUD OIL | 10.0 | 10.0 |
| PATCHOULI OIL | 79.5 | 79.5 |
| DIHYDROMYRCENOL | 60.0 | 60.0 |

-continued

| Odiferous substance(s) | Perfume oil A1 (Comparison) | Perfume oil A2 (As per invention) |
|---|---|---|
| ISORALDEINE ® ((E)-3-methyl-4-(2,6,6-trimethyl-cyclohex-2-enyl)-but-3-en-2-one) | 20.0 | 20.0 |
| EBANOL (3-METHYL-5-(2,2,3-TRIMETHYL-3-CYCLOPENTENYL)-4E/Z-PENTEN-2-ONE) | 15.0 | 15.0 |
| GLOBALIDE ® (E/Z-11-PENTADECEN-1,15-OLIDE) | 60.0 | 60.0 |
| ALPHA-HEXYL CINNAMALDEHYDE | 40.0 | 40.0 |
| COUMARIN | 20.0 | 20.0 |
| LILIAL ® (2-METHYL-3-(4-TERT.-BUTYLPHENYL)-PROPANAL) | 30.0 | 30.0 |
| LINALOOL | 20.0 | 20.0 |
| LINALYL ACETATE | 30.0 | 30.0 |
| VANILLIN | 20.0 | 20.0 |
| LYRAL ® (4-FORMYL-2-(4-HYDROXY-4-METHYL-PENTYL)-CYCLOHEXENE) | 40.0 | 40.0 |
| HEDION ® (METHYL-CIS/TRANS-DIHYDROJASMONATE) | 30.0 | 30.0 |
| EVERNYL ® (2,4-DIHYDROXY-3,6-DIMETHYL-BENZOIC ACID METHYL ESTER) | 5.0 | 5.0 |
| CEDRAMBER (CEDRYL METHYL ETHER) | 20.0 | 20.0 |
| ISO E SUPER ® (3-ACETYL-3,4,10,10-TETRAMETHYL-1(6)-BICYCLO[4.4.0]DECENE) | 150.0 | 150.0 |
| GERANIUM BASE | 20.0 | 20.0 |
| BERGAMOT BASE | 80.0 | 80.0 |
| WORMWOOD OIL | 10.0 | 10.0 |
| GALBANUM OIL 10% in DPG | 15.0 | 15.0 |
| AMBROCENIDE ® 0.1% in DPG | 20.0 | 20.0 |
| CYCLOGALBANAT ® 10% in DPG (CYCLOHEXYLOXYACETIC ACID ALLYL ESTER) | 5.0 | 5.0 |
| CISTUS OIL 10% in DPG | 10.0 | 10.0 |
| SPEARMINT OIL 10% in DPG | 10.0 | 10.0 |
| AURELIONE (E/Z-7/8-CYCLOHEXADECENONE) | 120.0 | 120.0 |
| AMBROXIDE | 5.0 | 5.0 |
| MANDARIN OIL | 5.0 | 5.0 |
| LAVANDIN OIL GROSSO | 30.0 | 30.0 |
| LEMON OIL | 20.0 | 20.0 |
| 4-n-DECYL PYRIDINE | | 0.5 |
| | 999.5 | 1,000.0 |

The proportion of 0.05% 4-decyl pyridine in the perfume oil S2 intensifies (at a dosing of 0.5% of the perfume oil in the shampoo) the fruity peach/apricot character and also lends the overall composition a further exotic tropical fruitiness. Furthermore, the composition as a whole appears to be more harmonious and rounded.

Example 2.5

Shower Gel

| Material | Producer | INCI name | Wt % |
|---|---|---|---|
| Deionized water | | Water | 76.3 |
| Plantacare PS 10 | Cognis Deutschland GmbH | Sodium laureth sulfate, lauryl glucoside | 20.0 |

-continued

| Material | Producer | INCI name | Wt % |
|---|---|---|---|
| Dragocid liquid | Symrise | Phenoxyethanol, methylparaben, ethylparaben, butylparaben, propylparaben, isobutylparaben | 0.5 |
| Sodium chloride | | Sodium chloride | 1.4 |
| Citric acid monohydrate crystalline | | Citric acid | 1.3 |
| Perfume oil D1 or D2 | Symrise | Perfume (Fragrance) | 0.5 |

Perfume Oils for this Shower Gel

| Odiferous substance(s) | Perfume oil D1 (Comparison) | Perfume oil D2 (As per invention) |
|---|---|---|
| CASSIS BASE | 10.0 | 10.0 |
| CLOVE BUD OIL | 5.0 | 5.0 |
| PATCHOULI OIL | 5.0 | 5.0 |
| DIHYDROMYRCENOL | 60.0 | 60.0 |
| HEXYL SALICYLATE | 20.0 | 20.0 |
| HEDION ® (METHYL-CIS/TRANS-DIHYDROJASMONATE) | 210.0 | 210.0 |
| ORANGE OIL | 25.0 | 25.0 |
| GLOBALIDE ® (E/Z-11-PENTADECEN-1,15-OLIDE) | 20.0 | 20.0 |
| POLYSANTOL ® (3,3-DIMETHYL-5-(2,2,3-TRIMETHYL-3-CYCLOPENTENYL)-4-PENTEN-2-OL) | 5.0 | 5.0 |
| LAVANDIN OIL GROSSO | 20.0 | 20.0 |
| YSAMBER ® K (ISOLONGIFOLANONE ETHANEDIOL KETAL) | 20.0 | 20.0 |
| ALPHA-HEXYL CINNAMALDEHYDE | 100.0 | 100.0 |
| LILIAL ® (2-METHYL-3-(4-TERT.-BUTYLPHENYL)-PROPANAL) | 50.0 | 50.0 |
| LINALOOL | 60.0 | 60.0 |
| LINALYL ACETATE | 50.0 | 50.0 |
| TERPINEOL | 20.0 | 20.0 |
| ETHYLENE BRASSYLATE (BRASSYLIC ACID ETHANEDIOL ESTER) | 20.0 | 20.0 |
| ALLYL AMYL GLYCOLATE (2-METHYLBUTOXY-ACETIC ACID ALLYL ESTER) | 10.0 | 10.0 |
| ISO E SUPER ® (3-ACETYL-3,4,10,10-TETRAMETHYL-1(6)-BICYCLO[4.4.0]DECENE) | 50.0 | 50.0 |
| KEPHALIS (3,3,5,5-TETRAMETHYL-4-(1-ETHOXYVINYL)-CYCLOHEXANONE) | 5.0 | 5.0 |
| BERGAMOT BASE | 100.0 | 100.0 |
| FLORALOZONE (2-METHYL-2-(4-ETHYLBENZYL)-PROPANAL | 10.0 | 10.0 |
| MANDARIN ALDEHYDE 10% in TEC (2E-DODECENAL) | 5.0 | 5.0 |
| LIGUSTRAL ® 10% in DPG (TRANS-2,4-DIMETHYL-1-FORMYL-3-CYCLOHEXENE) | 10.0 | 10.0 |
| ALPHA-DAMASCONE 1% in DPG ((E/Z)-1-(2,6,6-trimethyl-cyclohex-2-enyl)-but-2-en-1-one) | 20.0 | 20.0 |
| FARENAL ® 1% in DPG (2,6,10-TRIMETHYL-9-UNDECENAL) | 20.0 | 20.0 |
| LEAFOVERT ® 10% in DPG (CARBONIC ACID-3Z-HEXENYL METHYL ESTER) | 20.0 | 20.0 |
| CALONE ® 1951 10% in DPG (7-METHYL-3,4-DIHYDRO-3-BENZODIOXEPINONE) | 30.0 | 30.0 |
| 4-n-DECYL PYRIDINE 1% in DPG | | 20.0 |
| | 980.0 | 1,000.0 |

The proportion of 0.02% 4-decyl pyridine in the perfume oil D2 (at a dosing of 0.5% of the perfume oil in the shower gel) boosts (intensifies) the watery-fresh head note of the perfume oil composition and also lends the aromatic, woody, masculine scent greater power and fullness.

Example 2.6

Fine Fragrance

| Odiferous substance(s) | Perfume oil F1 (Comparison) | Perfume oil F2 (As per invention) |
|---|---|---|
| BRAHMANOL ® (2-METHYL-4-(2,2,3-TRIMETHYL-3-CYCLOPENTENYL)-BUTANOL) | 5.0 | 5.0 |
| AMBROCENIDE ® 10% in DPG | 2.0 | 2.0 |
| DIHYDROMYRCENOL | 40.0 | 40.0 |
| HELIONAL (2-PIPERONYL-PROPANAL) | 10.0 | 10.0 |
| LEMON OIL | 30.0 | 30.0 |
| GERANIOL | 5.0 | 5.0 |
| IRALDEIN GAMMA ((E)-3-methyl-4-(2,6,6-trimethyl-cyclohex-2-enyl)-but-3-en-2-one) | 20.0 | 20.0 |
| GLOBALIDE ® (E/Z-11-PENTADECEN-1,15-OLIDE) | 50.0 | 50.0 |
| CITRONELLA OIL | 5.0 | 5.0 |
| YSAMBER ® K (ISOLONGIFOLANONE ETHANEDIOL KETAL) | 90.0 | 90.0 |
| LILIAL ® (2-METHYL-3-(4-TERT.-BUTYLPHENYL)-PROPANAL) | 30.0 | 30.0 |
| LINALOOL | 30.0 | 30.0 |
| LINALYL ACETATE | 50.0 | 50.0 |
| HEDION ® (METHYL-CIS/TRANS-DIHYDROJASMONATE) | 100.0 | 100.0 |
| CIS-3-HEXENOL | 1.0 | 1.0 |
| CIS-3-HEXENYL ACETATE | 1.0 | 1.0 |
| ETHYL LINALOOL | 20.0 | 20.0 |
| CALONE ® 1951 (7-METHYL-3,4-DIHYDRO-3-BENZODIOXEPINONE) | 2.0 | 2.0 |
| GALAXOLIDE ® 50% in IPM (1,1,2,3,3,8-hexamethyl-1,2,3,5,7,8-hexahydro-6-oxa-cyclopenta[b]naphthalene) | 100.0 | 100.0 |
| BERGAMOT BASE | 50.0 | 50.0 |
| ISO E SUPER ® (3-ACETYL-3,4,10,10-TETRAMETHYL-1(6)-BICYCLO[4.4.0]DECENE) | 175.0 | 175.0 |
| PATCHOULI OIL | 10.0 | 10.0 |
| COSTUS BASE 1% in DPG | 5.0 | 5.0 |
| COUMARIN 10% in DPG | 5.0 | 5.0 |
| CASTOREUM BASE 10% in DPG | 1.0 | 1.0 |
| MANZANATE 1% in DPG (2-METHYL-PENTANOIC ACID ETHYL ESTER) | 3.0 | 3.0 |
| PARMANYL ® 10% in DPG (2-(3Z-HEXENYLOXY)-ETHYL CYANIDE) | 9.0 | 9.0 |
| VANILLIN 10% in DPG | 5.0 | 5.0 |
| ALPHA-DAMASCONE 10% in DPG ((E/Z)-1-(2,6,6-trimethyl-cyclohex-2-enyl)-but-2-en-1-one) | 3.0 | 3.0 |
| EUGENOL 10% in DPG | 5.0 | 5.0 |
| VERTOCITRAL 10% in DPG (TRANS-2,4-DIMETHYL-1-FORMYL-3-CYCLOHEXENE) | 2.0 | 2.0 |
| ZIBETH BASE 10% in DPG | 3.0 | 3.0 |
| GERANYL ACETATE 10% in DPG | 5.0 | 5.0 |
| BETA-DAMASCONE 10% in DPG ((E/Z)-1-(2,6,6-trimethyl-cyclohex-1-enyl)-but-2-en-1-one) | 2.0 | 2.0 |
| L-CARVONE 10% in DPG | 5.0 | 5.0 |
| CEYLON CINNAMON OIL 10% in DPG | 5.0 | 5.0 |
| AURELIONE (E/Z-7-/8-CYCLOHEXADECENONE) | 20.0 | 20.0 |
| AMBROXIDE | 10.0 | 10.0 |
| GLOBANONE ® (E/Z-8-CYCLOHEXADECENONE) | 50.0 | 50.0 |

-continued

| Odiferous substance(s) | Perfume oil F1 (Comparison) | Perfume oil F2 (As per invention) |
|---|---|---|
| STYROLYL ACETATE | 1.0 | 1.0 |
| CARDAMOM OIL (from GUATEMALA) | 1.0 | 1.0 |
| MELONAL ® | 1.0 | 1.0 |
| BENZYL SALICYLATE | 30.0 | 30.0 |
| AGRUMEX ® | 3.0 | 3.0 |
| 4-DECYL PYRIDINE 0.01% in DPG | | 10.0 |
| | 1,000.0 | 1,010.0 |

The proportion of 0.001% 4-decyl pyridine in perfume oil F2 (at a dosing of 12% of the perfume oil in ethanol) intensifies the transparent fresh head note and lends this masculine fragrance a greater radiance.

Example 2.7

Fabric Conditioner

| Material | Producer | Chemical name | Function | Wt % |
|---|---|---|---|---|
| Deionized water | | Water | Solvent | 72.4 |
| Rewoquat WE 18 | Evonic Goldschmidt GmbH | Dialkyl ester ammonium etho-sulfate | Cationic surfactant | 16.6 |
| Mergal K9N | Honeywell Austria GmbH | 5-chloro-2-methyl-3-(2H)-isothiazolone and 2-methyl-3-(2H)-isothiazolone | Preservative | 0.10 |
| Dow Corning 1520 Antifoam | Dow Corning GmbH, Germany | Polydimethyl-siloxane | Defoamer | 0.30 |
| Magnesium chloride 1% solution | | Magnesium chloride solution | Thickener | 10.00 |
| Perfume oil W1 or W2 | Symrise | | Perfume (fragrance) | 0.60 |

Perfume Oils for this Fabric Conditioner:

| Odiferous substance(s) | Perfume oil W1 (Comparison) | Perfume oil W2 (As per invention) |
|---|---|---|
| AMBROCENIDE ® 10% in DPG | 5.0 | 5.0 |
| DIHYDROMYRCENOL | 80.0 | 80.0 |
| HERBAFLORAT (ACETIC ACID TRI-CYCLO[5.2.1.0]-4-DECEN-8-YL ESTER) | 80.0 | 80.0 |
| HEXYL SALICYLATE | 100.0 | 100.0 |
| ALDEHYDE C8 (n-Octanal) | 10.0 | 10.0 |
| UNDECAVERTOL (4-METHYL-3-DECEN-5-OL) | 10.0 | 10.0 |
| MAJANTOL ® (2-(3-methyl-benzyl)-2-methyl-PROPANOL) | 50.0 | 50.0 |
| ALPHA-HEXYL CINNAMALDEHYDE | 70.0 | 70.0 |
| DIMETHYL BENZYL CARBINYL ACETATE | 15.0 | 15.0 |
| PHENYLETHYL ALCOHOL | 35.0 | 35.0 |
| HEDIONE ® (METHYL-CIS/TRANS-DIHYDROJASMONATE) | 30.0 | 30.0 |
| ISORALDEINE ® 70 ((E)-3-methyl-4-(2,6,6-trimethyl-cyclohex-2-enyl)-but-3-en-2-one) | 50.0 | 50.0 |

-continued

| Odiferous substance(s) | Perfume oil W1 (Comparison) | Perfume oil W2 (As per invention) |
|---|---|---|
| HERBYL PROPIONATE (PROPIONIC ACID TRICYCLO[5.2.1.0]-5(6)-DECEN-2-YLESTER) | 40.0 | 40.0 |
| ISO E SUPER ® (3-ACETYL-3,4,10,10-TETRAMETHYL-1(6)-BICYCLO[4.4.0]DECENE) | 120.0 | 120.0 |
| SYMROSE ® (4-(3-METHYL-BUTYL)-TRANS/CIS-CYCLOHEXANOL) | 50.0 | 50.0 |
| PHENOXANOL (3-METHYL-5-PHENYL-PENTANOL) | 20.0 | 20.0 |
| ALPHA-DAMASCONE 1% in DPG ((E/Z)-1-(2,6,6-trimethyl-cyclohex-2-enyl)-but-2-en-1-one) | 20.0 | 20.0 |
| NEROLIONE ® (2-ACETYL-3-METHYL-BENZOFURAN) | 5.0 | 5.0 |
| ORYCLON ® (ACETIC ACID-TRANS-4-TERT.-BUTYL CYCLOHEXYL ESTER) | 100.0 | 100.0 |
| AGRUMEX (ACETIC ACID-2-TERT.-BUTYL CYCLOHEXYL ESTER) | 40.0 | 40.0 |
| PATCHOULI OIL | 50.0 | 50.0 |
| HELVETOLIDE ® (PROPIONIC ACID-2-(1-(3,3-DIMETHYL CYCLOHEXYL)-ETHOXY-2-METHYL PROPYL ESTER) | 10.0 | 10.0 |
| 4-DECYL PYRIDINE | | 10.0 |
| | 990.0 | 1,000.0 |

At a dosing of 0.6% of the perfume oil W2 in the fabric conditioner the proportion of 1.0% 4-decyl pyridine contained therein brings about a harmonization of the fresh-flowery composition and also greatly increases the sought-after violet character.

Example 2.8

Transparent Deodorant Sticks (Formulations A, B) or Deodorant Cream Sticks (Formulations C, D)

| Components | A Wt % | B Wt % | C Wt % | D Wt % |
|---|---|---|---|---|
| Aluminium zirconium tetrachlorohydrate-glycine complex | 25.00 | 20.00 | 25.00 | 20.00 |
| Dimethicone (10 Cst) | — | — | 5.00 | 5.00 |
| Cyclopentasiloxane | — | 0.50 | 1.00 | 0.50 |
| Petrolatum | 5.00 | 4.70 | 5.00 | 5.00 |
| Ozocerite | 1.00 | 1.50 | — | — |
| Stearyl alcohol | 12.00 | 12.00 | — | — |
| 2-butyloctanic acid | 0.50 | — | 0.50 | — |
| Wax | — | — | 1.25 | 1.25 |
| PPG-14 butyl ether | 9.00 | 9.00 | — | — |
| Hardened rapeseed oil | — | — | 5.00 | 5.00 |
| Silicon dioxide | — | — | 1.00 | — |
| Farnesol | 0.25 | — | 0.25 | — |
| Paraffin oil | 0.50 | 0.50 | — | — |
| Hydrogenated castor oil (castor wax) | 3.50 | 3.50 | — | — |
| Talc | 4.00 | 4.00 | — | — |
| Behenyl alcohol | 0.20 | 0.20 | — | — |
| d-Panthenyl triacetate | 1.00 | 1.00 | — | — |

-continued

| Components | A Wt % | B Wt % | C Wt % | D Wt % |
| --- | --- | --- | --- | --- |
| Preservative | q.s. | q.s. | q.s. | q.s. |
| Perfume oil S2 from example 2.4 | 1.50 | — | 1.15 | — |
| Perfume oil C2 from example 2.2 | | 0.90 | — | 0.75 |
| Water | To 100 | To 100 | To 100 | To 100 |

PPG: Polypropylene glycol

Example 2.9

Antiperspirant Roll-On

| Components | Wt % | Wt % |
| --- | --- | --- |
| Caprylyl trimethicone (SilCare TM silicone 31 M 50) | 0.30 | 0.30 |
| Steareth-20 (GENAPOL TM HS 200) | 3.00 | 3.00 |
| Steareth-2 (GENAPOL TM HS 020) | 1.50 | 1.50 |
| Dicaprylyl ether (Cetiol TM OE) | 2.00 | 2.00 |
| Coco-caprylate/caprate (Cetiol TM LC) | 2.00 | 2.00 |
| Glycerine | 2.00 | 2.00 |
| Glyceryl stearate (Cutina TM GMS) | 2.00 | 2.00 |
| Octyl dodecanol (Eutanol TM G) | 1.00 | 1.00 |
| Stearyl alcohol | 2.50 | 2.50 |
| Aluminium chlorohydrate according to Example 1 of EP 1321431 | 10.00 | 10.00 |
| Avocado extract *Persea gratissima* | 0.30 | 0.20 |
| Perfume oil D2 from example 2.5 | 0.50 | — |
| Perfume oil S2 from example 2.4 | — | 0.60 |
| Water | To 100 | To 100 |

Example 2.10

Antiperspirant Stick

| Components | Wt % | Wt % |
| --- | --- | --- |
| Phenyl trimethicone (SilCare TM Silicone 15 M 50) | 13.50 | 13.50 |
| Cetearyl alcohol | To 100 | To 100 |
| Cetiol CC (dicaprylyl carbonate) | 13.50 | 13.50 |
| Stearic acid | 3.50 | 3.50 |
| PEG-40 hydrogenated castor oil (Emulsogen TM HCO 040) | 4.10 | 4.10 |
| PEG-8 distearate (Cithrol 4 DS) | 4.10 | 4.10 |
| Petrolatum | 6.90 | 6.90 |
| Aluminium chlorohydrate | 13.80 | 13.80 |
| Aluminium zirconium trichlorohydrex Gly | 19.50 | 20.00 |
| Ethylhexyl glycerine (octoxy glycerine) | 0.30 | 0.20 |
| 4-methyl-4-phenyl-2-pentanol (Vetikol) | 0.25 | 0.10 |
| Perfume oil F2 from example 2.6 | 1.00 | — |
| Perfume oil S2 from example 2.4 | — | 0.80 |

Example 2.11

Aerosol Spray

| Components | Wt % | Wt % | Wt % |
| --- | --- | --- | --- |
| Octyldodecanol | 0.50 | — | 0.50 |
| Phenoxyethanol | — | — | 0.30 |

-continued

| Components | Wt % | Wt % | Wt % |
| --- | --- | --- | --- |
| 1,2-pentanediol | 1.00 | 1.00 | 0.50 |
| 1,2-hexanediol | 0.25 | 0.15 | 0.25 |
| 1,2-octanediol | 0.25 | 0.25 | 0.25 |
| Farnesol | — | 0.25 | 0.15 |
| Ethylhexyl glycerine (octoxy glycerine) | 0.50 | 0.30 | 0.50 |
| Perfume oil F2 from example 2.6 | 0.80 | — | 0.50 |
| Perfume oil D2 from example 2.5 | — | 1.15 | 0.50 |
| Ethanol | To 100 | To 100 | To 100 |

The mixture obtained after mixing together the components indicated in each case was filled into an aerosol container with a propane-butane mixture (2:7) in a ratio by weight of 2:3.

Example 2.12

O/W Lotion

| Components | Wt % | Wt % | Wt % |
| --- | --- | --- | --- |
| Paraffin oil | 5.00 | 5.00 | 5.00 |
| Isopropyl palmitate | 5.00 | 5.00 | 5.00 |
| Cetyl alcohol | 2.00 | 2.00 | 2.00 |
| Beeswax | 2.00 | 2.00 | 2.00 |
| Ceteareth-20 | 2.00 | 2.00 | 2.00 |
| PEG-20-glyceryl stearate | 1.50 | 1.50 | 1.50 |
| Glycerine | 3.00 | 3.00 | 3.00 |
| Phenoxyethanol | 0.50 | 0.50 | — |
| Parabens (mixture of methyl-, ethyl-, propyl-, butyl-, isobutylparaben) | — | — | 0.50 |
| Perfume oil D2 from example 2.5 | 1.00 | — | 0.80 |
| Perfume oil F2 from example 2.6 | — | 1.25 | — |
| Water | To 100 | To 100 | To 100 |

Example 2.13

Hair Conditioner with UV Protection

| Components | INCI name | Wt % | Wt % |
| --- | --- | --- | --- |
| Lanette O | Cetearyl alcohol | 4.00 | 4.00 |
| Dragoxat 89 | Ethylhexyl isononanoate | 4.00 | 4.00 |
| Emulsiphos | Potassium cetyl phosphate, hydrogenated palm glycerides | 0.50 | 0.50 |
| Natrosol 250 HR | Hydroxyethylcellulose | 0.25 | 0.25 |
| Neo Heliopan Hydro | Phenylbenzimidazole sulfonic acid | 2.00 | 2.00 |
| L-Arginine | Arginine | 1.20 | 1.20 |
| Benzophenone-4 | Benzophenone-4 | 0.50 | 0.50 |
| Neo Heliopan AP | Disodium phenyl dibenzimidazole tetrasulfonate | 0.50 | 1.00 |
| Edeta BD | Disodium EDTA | 0.05 | 0.05 |
| Dragocide liquid | Phenoxyethanol (and) methylparaben (and) butyparaben (and) ethyparaben (and) propylparaben | 0.80 | 0.80 |
| Dow Corning 949 cationic emulsion | Amodimethicone, cetrimonium chloride, trideceth-12 | 2.00 | 2.00 |
| Dow Corning 5200 | Laurylmethicone copolyol | 0.50 | 0.50 |

-continued

| Components | INCI name | Wt % | Wt % |
|---|---|---|---|
| Perfume oil C2 from example 2.2 | Perfume | 0.95 | — |
| Perfume oil S2 from example 2.4 | Perfume | | 1.25 |
| Water | Water (aqua) | To 100 | To 100 |

Example 2.14

Sun Protection Spray

| Part | Raw materials | INCI name | Wt % |
|---|---|---|---|
| A | Water, demineralized | Water (aqua) | 69.50 |
| | Glycerine | Glycerine | 4.00 |
| | 1,3 butylene glycol | Butylene glycol | 5.00 |
| | D-Panthenol | Panthenol | 0.50 |
| | Lara Care A-200 | Galactoarabinan | 0.25 |
| B | Baysilone oil M 10 | Dimethicone | 1.00 |
| | Edeta BD | Disodium EDTA | 0.10 |
| | Copherol 1250 | Tocopheryl acetate | 0.50 |
| | Cetiol OE | Dicaprylyl ether | 3.00 |
| | Neo Heliopan ® HMS | Homosalate | 5.00 |
| | Neo Heliopan ® AV | Ethylhexyl methoxycinnamate | 6.00 |
| | Neo Heliopan ® 357 | Butyl methoxydibenzoylmethane | 1.00 |
| | Corapan TQ | Diethylhexylnaphthalate | 2.00 |
| | Alpha Bisabolol | Bisabolol | 0.10 |
| | Pemulen TR-2 | Acrylates/C10-30 alkyl acrylate crosspolymer | 0.25 |
| C | Phenoxyethanol | Phenoxyethanol | 0.70 |
| | Solbrol M | Methylparaben | 0.20 |
| | Solbrol P | Propylparaben | 0.10 |
| D | NaOH, 10% | Sodium hydroxide | 0.60 |
| E | Perfume oil D2 from example 2.5 | Fragrance (perfume) | 0.20 |

Production Method

Part A: Dissolve the Lara Care A-200 in the other components while stirring.

Part B: Weigh in all the raw materials (except the Pemulen) and dissolve the crystalline substances by heating. Disperse the Pemulen. Add part B to part A and homogenize for 1 minute.

Parts C-E: add and homogenize for a further 1-2 minutes with the Ultra Turrax.

Example 2.15

Sun Protection Soft Cream (W/O), Sun Protection Factor SPF 40

| Part | Raw materials | INCI name | Wt % |
|---|---|---|---|
| A | Dehymuls PGPH | Polyglyceryl-2 dipolyhydroxystearate | 5.00 |
| | Copherol 1250 | Tocopheryl acetate | 0.50 |
| | Permulgin 3220 | Ozocerite | 0.50 |
| | Zinc stearate | Zinc stearate | 0.50 |
| | Tegosoft TN | C12-15 Alkyl benzoate | 10.00 |
| | Neo Heliopan ® E1000 | Isoamyl-p-methoxycinnamate | 2.00 |
| | Neo Heliopan ® 303 | Octocrylene | 5.00 |
| | Neo Heliopan ® MBC | 4-Methylbenzylidene camphor | 3.00 |
| | Zinc oxide, neutral | Zinc oxide | 5.00 |

-continued

| Part | Raw materials | INCI name | Wt % |
|---|---|---|---|
| B | Water, distilled | Water (aqua) | To 100 |
| | EDETA BD | Disodium EDTA | 0.10 |
| | Glycerine | Glycerine | 4.00 |
| | Phenoxyethanol | Phenoxyethanol | 0.70 |
| | Solbrol M | Methylparaben | 0.20 |
| | Solbrol P | Propylparaben | 0.10 |
| | Magnesium sulfate | Magnesium sulfate | 0.50 |
| C | Perfume oil F2 from example 2.6 | Perfume (fragrance) | 0.30 |

Production Method

Part A: Heat to approximately 85° C.

Part B: Heat to approximately 85° C. (excluding zinc oxide; disperse the zinc oxide with the Ultra Turrax).

Add B to A. Allow to cool while stirring.

Part C: add and then homogenize.

Example 2.16

Sun Protection Milk (W/O)

| Part | Raw materials | INCI name | Wt % |
|---|---|---|---|
| A | Dehymuls PGPH | Polyglyceryl-2 dipolyhydroxystearate | 3.00 |
| | Beeswax 8100 | Beeswax | 1.00 |
| | Monomuls 90-0-18 | Glyceryl oleate | 1.00 |
| | Zinc stearate | Zinc stearate | 1.00 |
| | Cetiol SN | Cetearyl isononanoate | 5.00 |
| | Cetiol OE | Dicaprylyl ether | 5.00 |
| | Tegosoft TN | C12-15 alkyl benzoate | 4.00 |
| | Vitamin E | Tocopherol | 0.50 |
| | Solbrol P | Propylparaben | 0.10 |
| | Neo Heliopan ® OS | Ethylhexyl salicylate | 5.00 |
| | Neo Heliopan ® AV | Ethylhexyl methoxycinnamate | 7.50 |
| | Uvinul ® T150 | Ethylhexyl triazone | 1.50 |
| B | Water, distilled | Water (Aqua) | To 100 |
| | Trilon BD | Disodium EDTA | 0.10 |
| | Glycerine | Glycerine | 5.00 |
| | Solbrol M | Methylparaben | 0.20 |
| | Phenoxyethanol | Phenoxyethanol | 0.70 |
| | Neo Heliopan ® AP 10% solution, neutralized with NaOH | Disodium phenyl dibenzimidazole tetrasulfonate | 15.00 |
| C | Perfume oil S2 from example 2.4 | Perfume (fragrance) | 0.25 |
| | Alpha bisabolol | Bisabolol | 0.10 |

Production Method

Part A: Heat to approximately 85° C.

Part B: Heat to approximately 85° C. Add B to A. Allow to cool while stirring.

Part C: Add and then homogenize.

Specific Embodiments

Specific embodiment one comprises an aroma- and/or odiferous substance mixture, containing one or more 4-$C_8$-$C_{12}$-alkyl pyridine(s) and one or more further odiferous or aromatic substance(s), wherein preferably the 4-$C_8$-$C_{12}$-alkyl pyridines are 4-n-$C_8$-$C_{12}$-alkyl pyridines and with particular preference are selected from the group comprising 4-n-octyl pyridine, 4-n-nonyl pyridine, 4-n-decyl pyridine, 4-n-undecyl pyridine, 4-n-dodecyl pyridine and mixtures of one or more of these substances.

Specific embodiment two comprises the mixture as in specific embodiment one, containing as 4-$C_8$-$C_{12}$-alkyl pyridines 4-n-decyl pyridine, optionally with one or more further 4-$C_8$-$C_{12}$-alkyl pyridine(s), preferably one or more further 4-n-$C_8$-$C_{12}$-alkyl pyridine(s).

Specific embodiment three comprises the mixture as in one of the preceding specific embodiments, containing the 4-$C_8$-$C_{12}$-alkyl pyridine(s) in a sensorially active mixture to convey, intensify or modify a marine odor;

strengthen the intensity of the mixture;

convey, modify or intensify the radiance, freshness and/or naturalness of the mixture;

round off the odor of the mixture;

intensify and/or modify an odor or taste, and or increase the substantivity or diffusivity of an odiferous substance or the odiferous substance mixture.

Specific embodiment four comprises the mixture as in one of the preceding specific embodiments, containing the 4-$C_8$-$C_{12}$-alkyl pyridine(s) in a total quantity of 0.000001 to 5 Wt %, preferably 0.00001 to 2 Wt % and particularly preferably 0.0001 to 1 Wt %, in each case with reference to the aromatic or odiferous substance mixture as a whole.

Specific embodiment five comprises a perfumed or aromatized product, containing a mixture according to one of the above specific embodiments, preferably a mixture containing 4-n-decyl pyridine.

Specific embodiment six comprises the product as in specific embodiment five, containing the mixture in a sensorially active quantity to convey, intensify or modify a marine odor;

strengthen the intensity of an odor of an odiferous substance;

convey, modify or intensify the radiance, freshness and/or naturalness of the odor of the product;

round off the product odor intensify and/or modify an odor or taste, and/or increase the substantivity or diffusivity of an odiferous substance or an odiferous substance mixture of the product.

Specific embodiment seven comprises the product as in specific embodiment five or six, wherein the product is selected from among cosmetic products and household products, preferably shampoos, fabric conditioners and/or washing powders.

Specific embodiment eight comprises a use of one or more 4-$C_8$-$C_{12}$-alkyl pyridine(s), in particular one or more 4-n-$C_8$-$C_{12}$-alkyl pyridine(s) to modify and/or intensify (boost) an odor and/or taste, preferably with one, a plurality or all of the flowery, fruity, marine and/or mossy notes;

convey, intensify or modify a marine odor;

strengthen the intensity of an odiferous substance mixture;

convey, modify or intensify the radiance, freshness and/or naturalness of an odiferous substance mixture;

round off the odor of an odiferous substance mixture;

intensify and/or modify an odor or taste, and/or increase the substantivity or diffusivity of an odiferous substance or an odiferous substance mixture.

Specific embodiment nine comprises the use as in specific embodiment eight of 4-n-octyl pyridine to convey, intensify or modify a marine odor;

convey, intensify or modify a marine odor with an ozone note, and/or convey, intensify or modify a seaweed odor.

Specific embodiment ten comprises the use as in specific embodiment eight of 4-n-nonyl pyridine to convey, intensify or modify a marine odor;

convey, intensify or modify a marine odor with an algae accompanying note;

convey, intensify or modify a marine odor with hazelnut aspects, and/or increase the diffusivity of an odiferous substance mixture, preferably an odiferous substance mixture with a marine odor.

Specific embodiment eleven comprises the use as in specific embodiment eight of 4-n-decyl pyridine to:

convey, intensify or modify a marine odor;

convey, intensify or modify a marine odor with accompanying notes of ozone, buttery diacetyl aspect and/or echoes of orange peel, and/or increase the diffusivity of an odiferous substance mixture, preferably an odiferous substance mixture with a marine odor.

Specific embodiment twelve comprises the use as in specific embodiment eight of 4-n-undecyl pyridine to convey, intensify or modify a marine odor;

convey, intensify or modify a marine odor with an accompanying note of mandarin, with an accompanying note of ozone and/or an accompanying note of fatty aldehydes, and/or increase the diffusivity of an odiferous substance mixture, preferably an odiferous substance mixture with a marine odor.

Specific embodiment thirteen comprises the use as in specific embodiment eight of 4-n-dodecyl pyridine to convey, intensify or modify a marine odor;

convey, intensify or modify a marine odor with an accompanying note of seaweed, citric aspects and/or a nutty-dusty note and/or increase the diffusivity of an odiferous substance mixture, preferably an odiferous substance mixture with a marine odor.

Specific embodiment fourteen comprises a method to convey, intensify or modify a marine odor;

strengthen the intensity of an odiferous substance mixture;

convey, modify or intensify the radiance, freshness and/or naturalness of an odiferous substance mixture;

round off the odor of an odiferous substance mixture;

intensify and/or modify an odor or taste and/or increase the substantivity or diffusivity of an odiferous substance or an odiferous substance mixture in each case in a product, comprising the bringing into contact, preferably blending, of one or more 4-$C_8$-$C_{12}$-alkyl pyridine(s), preferably 4-n-$C_8$-$C_{12}$-alkyl pyridines, in a sensorially active quantity with a product.

Specific embodiment fifteen comprises the method as in specific embodiment fourteen, wherein the 4-$C_8$-$C_{12}$-alkyl pyridine(s) is (are) or contains (contain) 4-n-decyl pyridine.

The invention claimed is:

1. A method for imparting a marine odor to a human comprising applying a composition comprising 0.000001 to 2 wt. % of one or more 4-$C_8$-$C_{12}$-alkyl pyridine(s) and one or more further odiferous or aromatic substance(s) to the human, and wherein the one or more 4-alkyl pyridine(s) is selected from the group consisting of 4-n-decyl pyridine, 4-n-undecyl pyridine, 4-n-dodecyl pyridine and mixtures thereof.

2. The method according to claim 1, wherein the composition further comprises at least one of a 4-n-$C_8$-$C_9$ alkyl pyridine(s).

3. The method according to claim 1, wherein the method imparts a marine odor with an algae accompanying note.

4. The method according to claim 1, wherein the method imparts a marine odor with hazelnut aspects.

5. The method according to claim 1, wherein the method imparts a marine odor with accompanying notes of ozone, buttery diacetyl and/or orange peel.

6. The method according to claim 1, wherein the method imparts a marine odor with accompanying notes of seaweed, citric aspects, and/or a nutty-dusty note.

7. The method according to claim 1, wherein the one or more 4-$C_8$-$C_{12}$-alkyl pyridine(s) is 4-n-decyl pyridine.

8. The method according to claim 1, wherein the one or more 4-$C_8$-$C_{12}$-alkyl pyridine(s) is a mixture of 4-$C_8$-$C_{12}$-alkyl pyridines.

9. The method according to claim 8, wherein the mixture comprises 4-n-decyl pyridine and one or more additional of 4-$C_8$-$C_{12}$-alkyl pyridine(s).

10. The method according to claim 1, wherein the composition is selected from the group consisting of an eau de perfume, an eau de toilette, an aftershave, an eau de cologne, a pre-shave product, a splash cologne, a perfumed freshening wipe, an aerosol, a spray, a solid or liquid soap, a shower gel, a shampoo, a shaving soap, a shaving foam, a bath oil, a cosmetic skin cream or lotion, a sun protection cream or lotion, an after-sun cream or lotion, a hand cream or lotion, a foot cream or lotion, a depilatory cream or lotion, an after-shave cream or lotion, a bronzing cream or lotion, a hair care product, a hair spray, a hair gel, a hair lotion, a hair rinse, a permanent or semi-permanent hair dye, a hair shaping agent, a hair tonic, a hair cream or lotion, a deodorant or antiperspirant, an underarm spray, a roll-on, a deodorant stick, a deodorant cream, and a decorative cosmetic product.

11. A composition which is a mixture of odiferous or aromatic substances comprising (i) 0.000001 to 2 wt. % of one or more 4-alkyl pyridine(s) and (ii) one or more further odiferous or aromatic substance(s), wherein the composition is appropriate for application to a human, imparts a marine odor, and wherein the one or more 4-alkyl pyridine(s) (i) is selected from the group consisting of 4-n-decyl pyridine, 4-n-undecyl pyridine, 4-n-dodecyl pyridine and mixtures thereof.

12. The composition according to claim 11, wherein the composition imparts a marine odor with an algae accompanying note.

13. The composition according to claim 11, wherein the composition imparts a marine odor with hazelnut aspects.

14. The composition according to claim 11, wherein the composition imparts a marine odor with accompanying notes of ozone, buttery diacetyl and/or orange peel.

15. The composition according to claim 11, wherein the composition imparts a marine odor with accompanying notes of seaweed citric aspects, and/or a nutty-dusty note.

16. Cosmetic products, comprising odiferous or aromatic mixtures according to claim 11.

17. Products for household, comprising odiferous or aromatic substance mixtures according to claim 11.

18. A household product according to claim 17, wherein the products are shampoos, softeners or washing powders.

* * * * *